(12) United States Patent
Palti et al.

(10) Patent No.: US 12,178,853 B2
(45) Date of Patent: Dec. 31, 2024

(54) METHOD AND COMPOUNDS FOR TREATING DIABETES AND ASSOCIATED METABOLIC DISEASES

(71) Applicant: Betavive Ltd., Haifa (IL)

(72) Inventors: Yoram Palti, Haifa (IL); Dotan Zuri, Shekhanya (IL)

(73) Assignee: Betavive Ltd., Tirat Carmel (IL)

( * ) Notice: Subject to any disclaimer, the term of this patent is extended or adjusted under 35 U.S.C. 154(b) by 0 days.

(21) Appl. No.: 17/499,296

(22) Filed: Oct. 12, 2021

(65) Prior Publication Data

US 2022/0111011 A1    Apr. 14, 2022

Related U.S. Application Data

(60) Provisional application No. 63/234,862, filed on Aug. 19, 2021, provisional application No. 63/090,943, filed on Oct. 13, 2020.

(51) Int. Cl.
*A61K 38/30* (2006.01)
*A61P 3/10* (2006.01)

(52) U.S. Cl.
CPC ............... *A61K 38/30* (2013.01); *A61P 3/10* (2018.01)

(58) Field of Classification Search
CPC ............... A61K 38/30; A61P 3/10; A61P 3/08
See application file for complete search history.

(56) References Cited

U.S. PATENT DOCUMENTS

| | | | |
|---|---|---|---|
| 4,160,452 A | 7/1979 | Theeuwes | |
| 4,256,108 A | 3/1981 | Theeuwes | |
| 4,265,874 A | 5/1981 | Bonsen et al. | |
| 7,396,918 B2 * | 7/2008 | Glass | A61P 31/18 536/23.4 |
| 9,146,230 B2 | 9/2015 | Paiti | |
| 2006/0166328 A1 * | 7/2006 | Glass | A61P 3/10 435/325 |
| 2007/0172453 A1 | 7/2007 | Geenen | |
| 2020/0376028 A1 | 12/2020 | Palti | |
| 2021/0315914 A1 * | 10/2021 | Alberini | A61K 31/70 |

FOREIGN PATENT DOCUMENTS

| | | | |
|---|---|---|---|
| EP | 2900255 A2 | 8/2015 | |
| EP | 3549598 A1 | 10/2019 | |
| WO | WO 91/03253 | * | 3/1991 |
| WO | 9827813 A1 | 7/1998 | |
| WO | 2004019965 A2 | 3/2004 | |
| WO | 2006112737 A1 | 10/2006 | |
| WO | 2018189661 A2 | 10/2018 | |
| WO | 2020070540 A1 | 4/2020 | |

OTHER PUBLICATIONS

Bowie et al., 1990, Science 247: 1306-1310.*
Wells, 1990, Biochemistry 29:8509-8517.*
Casellas et al., "Insulin-like Growth Factor 2 Overexpression Induces Beta-Cell Dysfunction and Increases Beta-cell Susceptibility to Damage," The Journal of Biological Chemistry, vol. 290, No. 27, Jul. 2015.
Imai et al., "Insulin-Like Growth Factor 2 (IGF2) is Reduced in Diabetic Retina and Serum," ARVO Annual Meeting Abstract, Apr. 2010.
International Search Report and Written Opinion issued in application No. PCT/IB2021/059370 dated Jan. 24, 2022.
Jorgensen et al., "Calculation of Glucose Dose for Intraperitoneal Glucose Tolerance Tests in Lean and Obese Mice," Journal of the American Association for Laboratory Animal Science, vol. 56, No. 1, pp. 95-97, Jan. 2017.
Leighton et al., "A Practical Review of C-Peptide Testing in Diabetes," Diabetes Ther., vol. 8, pp. 475-487, May 2017.
Nair et al., "A simple practice guide for dose conversion between animals and human," J. Basic Clin Pharm., vol. 7, No. 2, pp. 27-31, Mar. 2016.
Bowie et al., "Deciphering the Message in Protein Sequences: Tolerance to Amino Acid Substitutions," Science, vol. 247, pp. 1306-1310, Mar. 1990.
International Search Report and Written Opinion issued in application No. PCT/IB2022/059757 dated Mar. 13, 2023.
Lee et al., "Vesiculin Derived from IGF-II drives increased islet cell mass in a mouse model of pre-diabetes," Islets, vol. 14, No. 1, pp. 14-22, Oct. 2021.
Wells, "Additivity of Mutational Effects in Proteins," Biochemistry, vol. 29, No. 37, pp. 8509-8517, Sep. 1990.
Williams et al., "Synthesis of the IGF-II-like hormone vesculin using regioselective formaton of disulfide bonds," Organic & Biomolecular Chemistry, vol. 11, No. 19, p. 3145, Jan. 2013.

* cited by examiner

*Primary Examiner* — Gyan Chandra
(74) *Attorney, Agent, or Firm* — Potomac Law Group, PLLC

(57) ABSTRACT

The disclosure provides for compounds, compositions, and methods of use thereof for treating diabetes (e.g., type 1 diabetes, type 2 diabetes). In some aspects, methods comprise administering first, second, third, fourth, and fifth daily doses of insulin-like growth factor 2 ("IGF-2") or a variant thereof to the subject at respective first, second, third, fourth, and fifth different times, wherein each of the daily doses comprises at least 65 µg of IGF-2. In other aspects, compounds, compositions, and methods containing IGF-2 or variants thereof are used for treating a disorder in a patient in need thereof, such as type 1 or type 2 diabetes.

7 Claims, 38 Drawing Sheets

Specification includes a Sequence Listing.

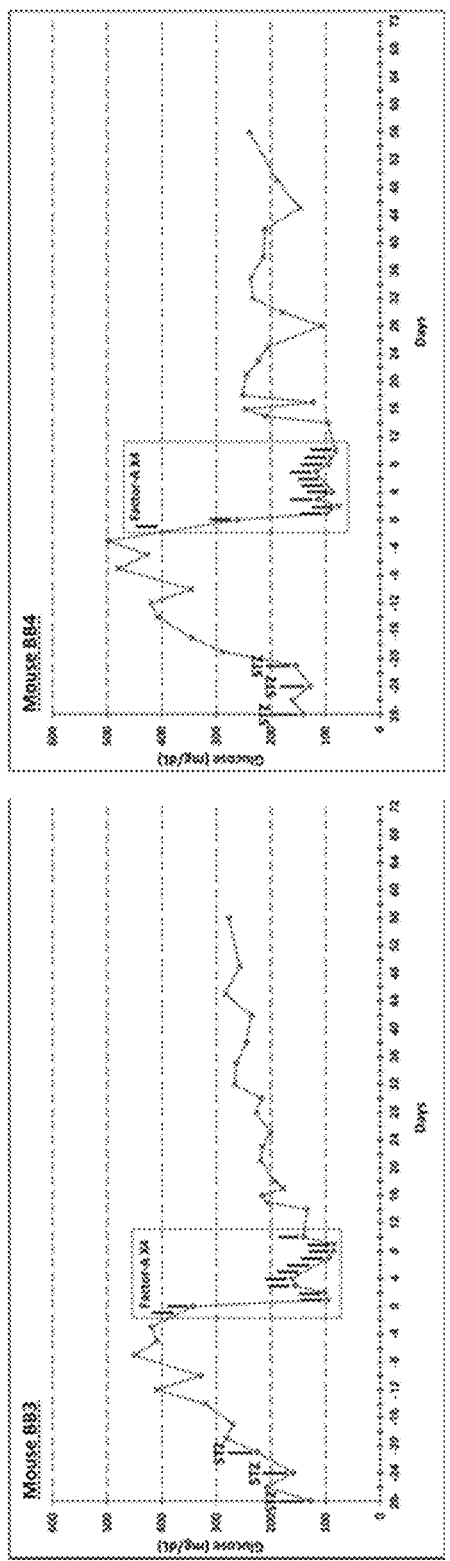
Figure 11A
Figure 11B
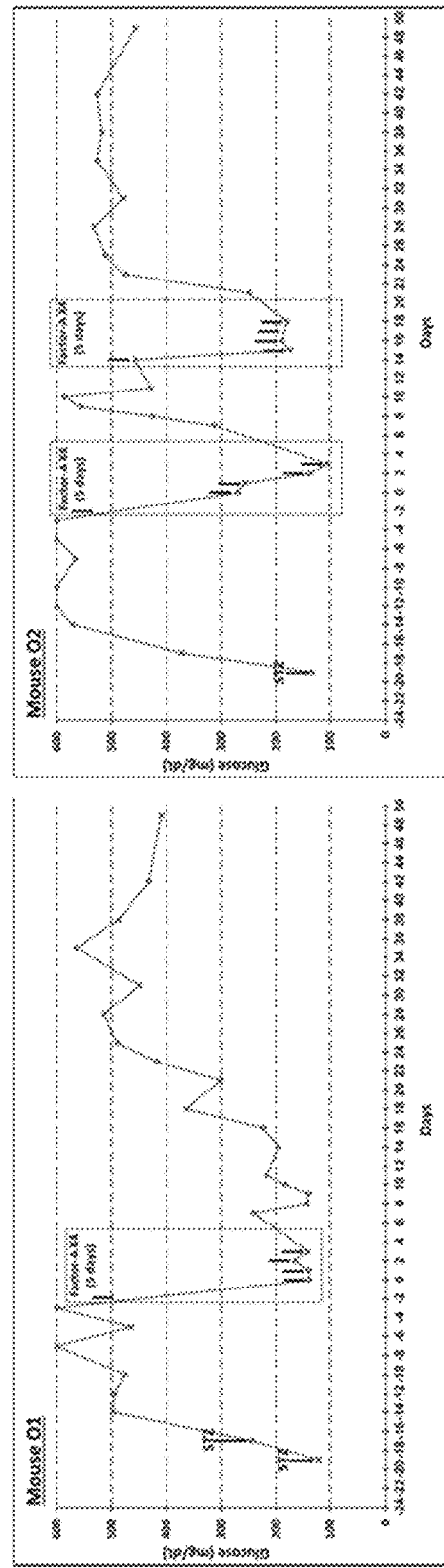
Figure 12A
Figure 12B

Figure 15 (slide 12)

Pancreas Islets stained for Insulin

Naïve mouse

SEQUENCE LISTING

```
<160> NUMBER OF SEQ ID NOS: 1

<210> SEQ ID NO 1
<211> LENGTH: 180
<212> TYPE: PRT
<213> ORGANISM: Homo sapiens

<400> SEQUENCE: 1

Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
```

```
               35                  40                  45
Gly Phe Tyr Phe Ser Arg Pro Ala Ser Arg Val Ser Arg Arg Ser Arg
                50                  55                  60

Gly Ile Val Glu Glu Cys Cys Phe Arg Ser Cys Asp Leu Ala Leu Leu
 65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
               100                 105                 110

Phe Phe Gln Tyr Asp Thr Trp Lys Gln Ser Thr Gln Arg Leu Arg Arg
               115                 120                 125

Gly Leu Pro Ala Leu Leu Arg Ala Arg Arg Gly His Val Leu Ala Lys
               130                 135                 140

Glu Leu Glu Ala Phe Arg Glu Ala Lys Arg His Arg Pro Leu Ile Ala
145                 150                 155                 160

Leu Pro Thr Gln Asp Pro Ala His Gly Gly Ala Pro Pro Glu Met Ala
               165                 170                 175

Ser Asn Arg Lys
           180
```

METHOD AND COMPOUNDS FOR TREATING DIABETES AND ASSOCIATED METABOLIC DISEASES

CROSS-REFERENCE TO RELATED APPLICATIONS

This application claims priority to and the benefit of U.S. Provisional Patent Application No. 63/090,943 filed Oct. 13, 2020, and U.S. Provisional Patent Application No. 63/234,862 filed Aug. 19, 2021, which are hereby incorporated by reference in their entirety.

SEQUENCE LISTING

This application contains a Sequence Listing which has been submitted electronically in ASCII format and is hereby incorporated by reference in its entirety. Said ASCII copy, created on Oct. 12, 2021, is named 1462-0017SeqListing.txt and is 1,966 bytes in size.

BACKGROUND

Diabetes mellitus (DM), commonly referred to as diabetes, is a major worldwide medical problem. As of 2015, an estimated 415 million people had diabetes worldwide, with type 2 DM making up about 90% of the cases. This represents 8.3% of the adult population, with equal rates in both women and men. The incidence of DM is increasing in most of the world populations.

Diabetes is a group of metabolic diseases in which there are high blood sugar levels over a prolonged period. Symptoms of high blood sugar include frequent urination, increased thirst, and increased hunger. If left untreated, diabetes can cause many complications. Acute complications can include diabetic ketoacidosis, non-ketonic hyperosmolar coma, or death. Serious long-term complications include heart disease, stroke, chronic kidney failure, foot ulcers, and damage to the eyes.

Diabetes is due to, for example, the pancreas not producing enough insulin or to the cells of the body not responding properly to the insulin produced. There are three main types of diabetes mellitus.

Type 1 DM results from the pancreas's failure to produce enough insulin. This form was previously referred to as "insulin-dependent diabetes mellitus" (IDDM) or "juvenile diabetes". The cause is unknown.

Type 2 DM begins with insulin resistance, a condition in which cells fail to respond to insulin properly. As the disease progresses, a lack of insulin may also develop. This form was previously referred to as "non-insulin dependent diabetes mellitus" (NIDDM) or "adult-onset diabetes." The primary cause of Type 2 DM is excessive body weight, and insufficient exercise.

Gestational diabetes is the third main form and occurs when pregnant women without a previous history of diabetes develop high blood-sugar levels.

Type 1 DM can be managed with insulin injections. Type 2 DM may be treated with medications with or without insulin. Gestational diabetes usually resolves after the birth of the baby.

The use of insulin can require daily injections which are expensive and inconvenient for patients. In addition, the use of insulin can cause low blood sugar, headache, hunger, weakness, sweating, tremors, irritability, trouble concentrating, rapid breathing, fast heartbeat, fainting, or seizure. Insulin therapy requires ongoing, daily therapy to be effective.

SUMMARY OF THE INVENTION

Aspects described herein provide compositions and methods of treating diabetes and related conditions using insulin-like growth factor 2 ("IGF-2") or a variant thereof. In some instances, the treatment provides long-term results, which eliminates the need for ongoing daily injections and the side effects and expense of daily insulin therapy.

Aspects described herein provide methods of treating diabetes (and related conditions) in a subject in need of treatment by administering first, second, third, fourth, and fifth daily doses of IGF-2 or a variant thereof to the subject at respective first, second, third, fourth, and fifth different days, wherein each of the daily doses comprises at least 65 µg of IGF-2 or the variant thereof.

Further aspects provide methods of treating diabetes by administering IGF-2 or a variant thereof to a subject in need of treatment in an amount from about 65 µg/kg of a weight of the subject to about 1626 µg per kg of the weight of the subject.

Further aspects provide methods of lowering the blood level of glucose in a subject by administering IGF-2 or a variant thereof to a subject in need of treatment in an amount from about 65 µg/kg of a weight of the subject to about 813 µg per kg of the weight of the subject.

Further aspects provide pharmaceutical compositions comprising IGF-2 or a variant thereof in an amount sufficient to lower the blood glucose level of a subject to about normal levels compared to a subject that does not receive the IGF-2 or a variant thereof, and a pharmaceutically acceptable excipient.

Aspects described herein provide methods of treating diabetes in a subject in need of treatment. The method comprises administering a daily dose of IGF-2 or a variant thereof to the subject on each of N different days. In this aspect, N is at least 5, and both (a) N and (b) the daily dose of IGF-2 or the variant thereof that is administered to the subject on each of the N different days, are sufficiently high to (i) reduce the subject's glucose levels to about normal levels prior to an end of the N different days, and (ii) keep the subject's glucose levels at about normal levels for at least 10 days after the end of the N different days.

Aspects described herein provide methods of treating type 2 diabetes in a subject in need of treatment and having a weight. The method comprises administering first, second, third, fourth, and fifth daily doses of IGF-2 or a variant thereof to the subject on respective days, wherein each of the daily doses comprises at least 244 µg of IGF-2 or the variant thereof per kg of the weight.

Aspects described herein provide methods of preventing an onset of type 1 diabetes in a subject having a weight. The method comprises administering first, second, third, fourth, and fifth daily doses of IGF-2 or a variant thereof to the subject on respective days, wherein each of the daily doses comprises at least 65 µg of IGF-2 or a variant thereof per kg of the weight.

Further aspects described herein provide methods of increasing insulin levels in a bloodstream of a subject having diabetes and having a weight. The method comprises administering first, second, third, fourth, and fifth daily doses of IGF-2 or a variant thereof to the subject on respective days, wherein each of the daily doses comprises at least 65 µg of IGF-2 or a variant thereof per kg of the weight.

Aspects described herein provide methods of increasing a number of functional beta cells in a subject having diabetes and having a weight. The method comprises administering first, second, third, fourth, and fifth daily doses of IGF-2 or a variant thereof to the subject on respective days, wherein each of the daily doses comprises at least 65 μg of IGF-2 or a variant thereof per kg of the weight.

Yet further aspects described herein provide methods of preventing an onset of type 2 diabetes in a subject having a weight. The method comprises administering first, second, third, fourth, and fifth daily doses of IGF-2 or a variant thereof to the subject on respective days, wherein each of the daily doses comprises at least 65 μg of IGF-2 or a variant thereof per kg of the weight.

BRIEF DESCRIPTION OF THE DRAWINGS

FIGS. 11A, 11B, 12A, and 12B depict the exemplary blood glucose levels in four mice during experiments in which diabetes was induced with STZ and IGF-2 was provided to the mouse at the time points indicated at a daily dose of 12,000 μg/kg.

DESCRIPTION OF THE PREFERRED EMBODIMENTS

Figure 1:
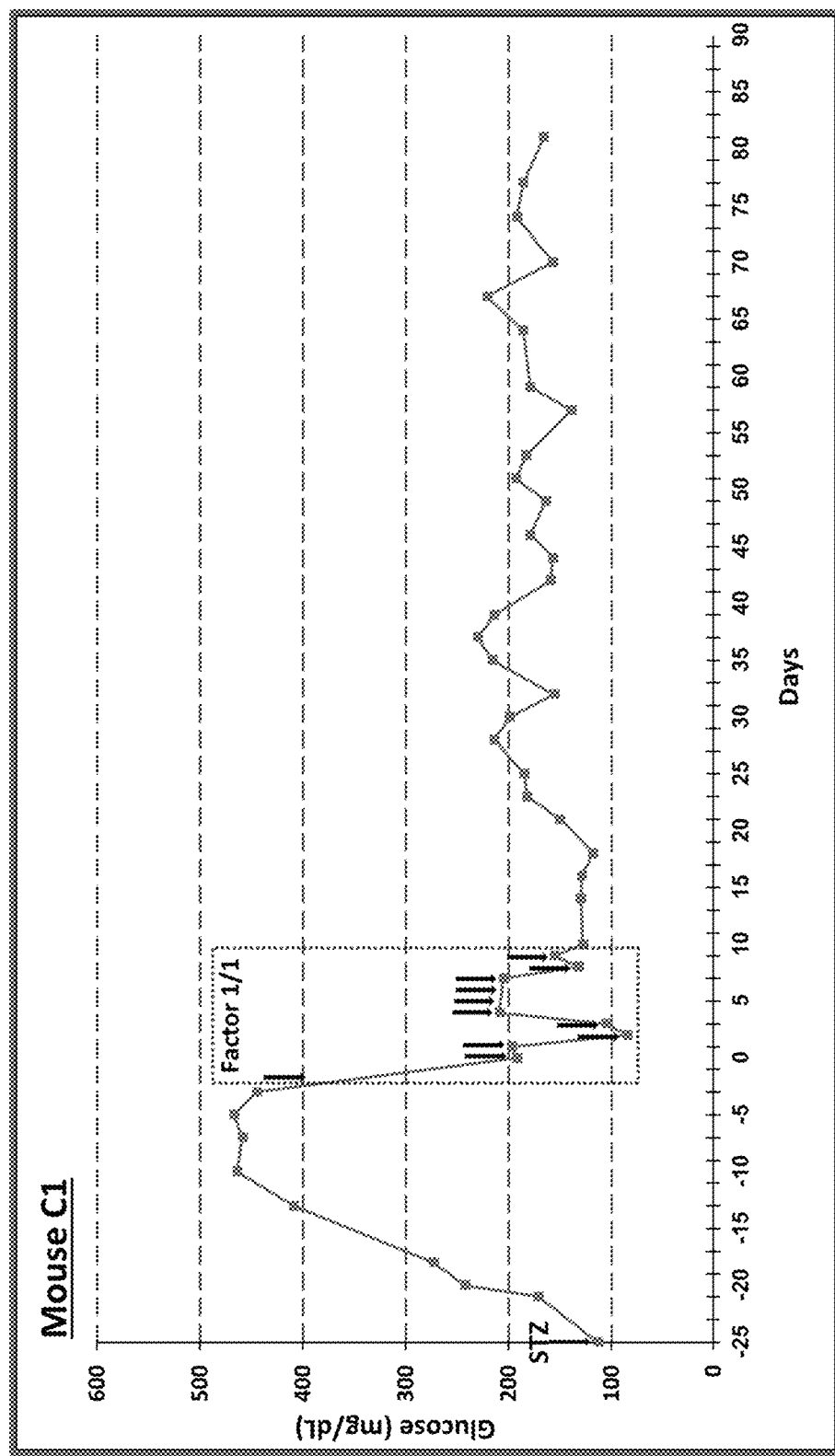
FIGS. 1-4 depict the blood glucose levels in four mice during an experiment in which diabetes was induced with streptozotocin (STZ) and IGF-2 was provided to the mouse at the time points indicated at a daily dose of 3,000 μg/kg (1/1 dose)
Figure 2:
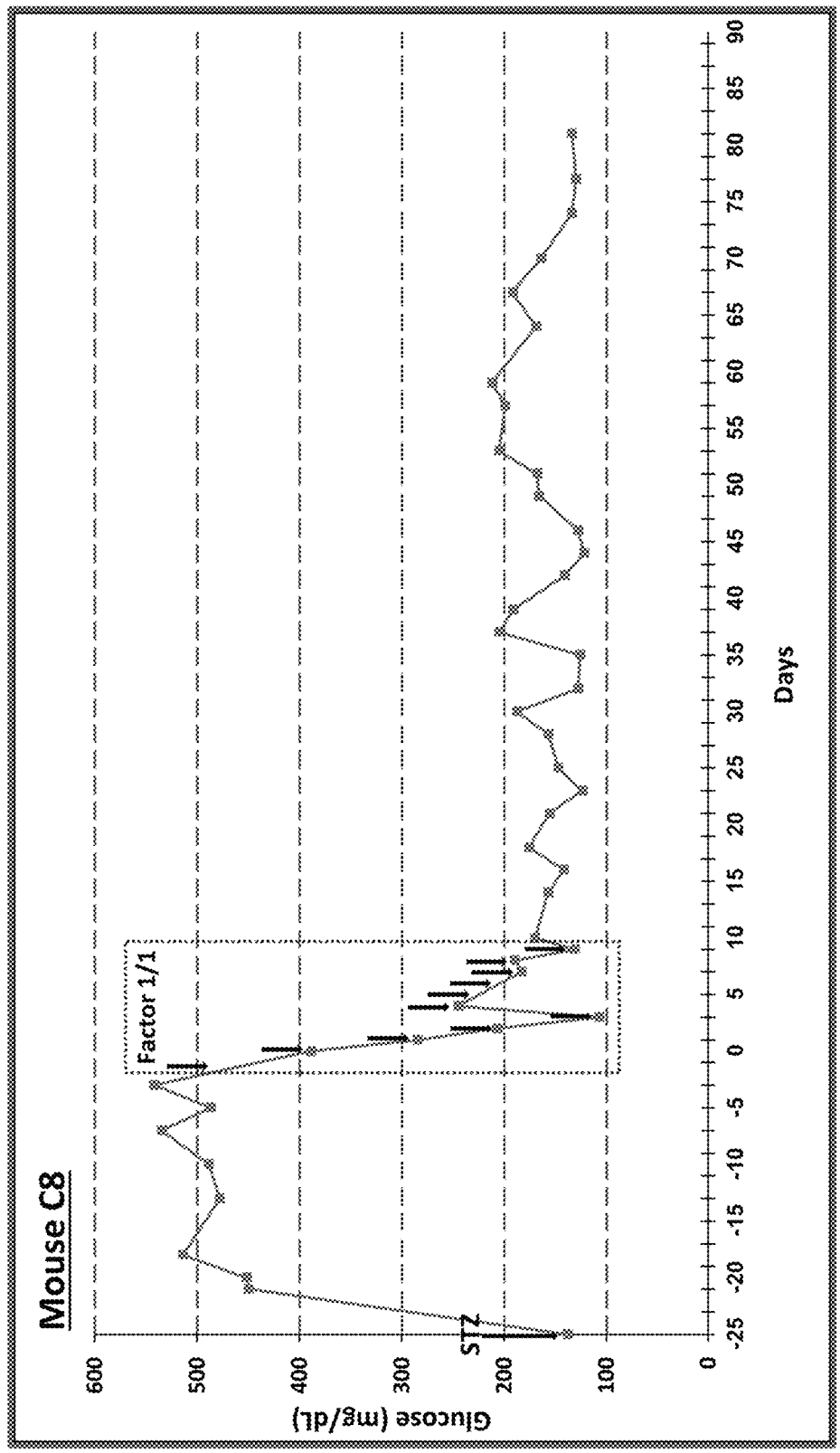
Figure 3:
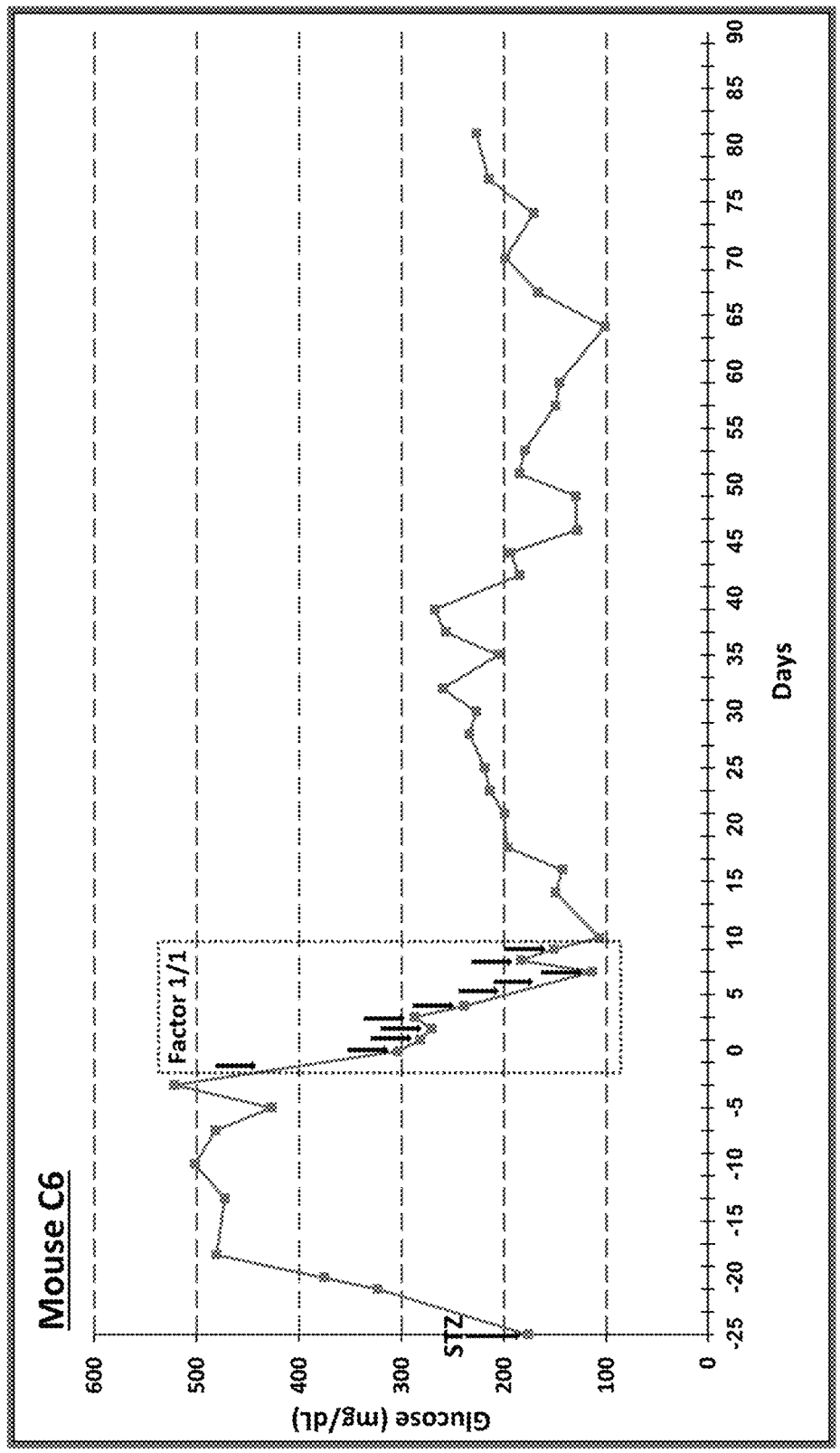
Figure 4:
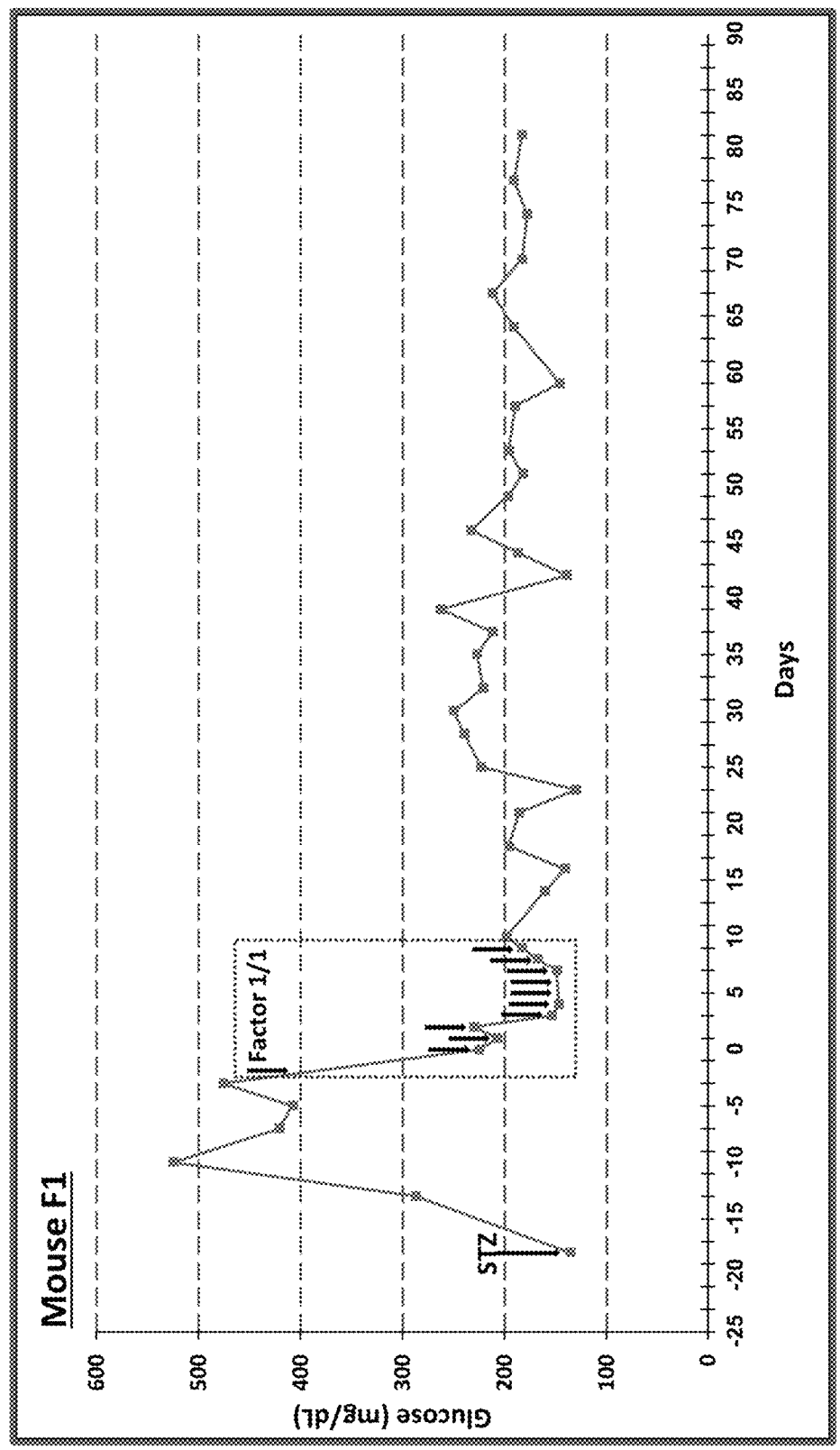

Aspects described herein provide methods of treating diabetes (and related conditions) in a subject in need of treatment by administering first, second, third, fourth, and fifth daily doses of IGF-2 or a variant thereof to the subject at respective first, second, third, fourth, and fifth different days, wherein each of the daily doses comprises at least 65 μg of IGF-2 or the variant thereof per kg of the weight. The term "normal levels" refers to levels at which the subject would not be considered to be in need of treatment if the glucose level was maintained (e.g., a glucose level in a human between about 60 and about 110 mg/dL).

The animal experiments described herein were conducted in mice using IGF-2 doses adapted for mice. It is expected that a human equivalent dose (HED) will be used to treat humans with IGF-2. In this aspect, the HED doses for IGF-2 and variants thereof were calculated in accordance with established U.S. Food and Drug Administration guidelines. Nair A B, Jacob S., *A simple practice guide for dose conversion between animals and human*, J Basic Clin Pharma 2016; 7:27-31. For example, a HED IGF-2 dose based on a mouse IGF-2 dose is obtained by dividing the mouse dose by 12.3. In this aspect, a mouse IGF-2 dose of 800 μg/kg corresponds to a 65 μg/kg dose in humans, a mouse IGF-2 dose of 3000 μg/kg corresponds to a 244 μg/kg dose in humans, and a mouse IGF-2 dose of 12,000 μg/kg corresponds to a 976 μg/kg dose in humans. The HED for IGF-2 and variants thereof, as described herein, can be calculated by dividing the mouse dose by 12.3. In another aspect, the dose of IGF-2 and variants thereof can be at least 800, 3,000, or 12,000 μg/kg in, for example, a human.

As described herein, IGF-2 and variants thereof offer a range of treatment options for maintaining "normoglycemia" (i.e., blood glucose levels in a normal range) in a subject having hyperglycemia, type I and II diabetes, and related autoimmune disorders. Without being bound by theory, and based on data described herein, IGF-2 increases blood serum insulin levels and the number of functional beta pancreatic cells. Importantly, these effects can be used for short term treatment (e.g., 30 days or less) or long term treatment. In addition, the normoglycemic effect is maintained in many cases even after treatment is stopped. In this aspect, treatment with IGF-2 as described herein can be used to treat conditions such as type II diabetes and delay or prevent the onset of conditions such as type I diabetes. In addition, treatment with IGF-2 and variants thereof, as described herein, can be used to prevent onset of type II diabetes. For example, IGF-2 treatment can be used in subjects at risk for diabetes or diagnosed as being prediabetic to prevent or eliminate onset of type II diabetes.

The term "diabetes" includes diabetes generally, type I diabetes, type II diabetes, and gestational diabetes. "Conditions related to diabetes" includes abnormal insulin resistance, abnormal blood glucose level, abnormal insulin level, hyperinsulinemia, glycosylated hemoglobin level, metabolic syndrome, increased blood pressure, high blood sugar, excess body fat around the waist, or abnormal cholesterol or triglyceride levels or a combination thereof. IGF-2 and variants can be used to treat conditions related to diabetes.

The term "IGF-2" refers to human insulin-like growth factor 2 and variants thereof. IGF-2 includes SEQ ID NO. 1 and variants having at least 95% homology with SEQ ID NO. 1.

In some instances, the first, second, third, fourth, and fifth different days occur on different consecutive days.

In some instances, sixth, seventh, and eighth daily doses of IGF-2 or a variant thereof can be administering sixth, seventh, eighth, ninth, and tenth daily doses of IGF-2 or a variant thereof to the subject at respective sixth, seventh, eighth, ninth, and tenth different days, wherein the first, second, third, fourth, fifth, sixth, seventh, eighth, ninth, and tenth different days occur on consecutive days.

The methods can further comprise administering sixth, seventh, eighth, ninth, and tenth daily doses of IGF-2 or a variant thereof to the subject at respective sixth, seventh, eighth, ninth, and tenth different days, wherein the first, second, third, fourth, fifth, sixth, seventh, eighth, ninth, and tenth different days occur on consecutive days.

In some instances, each of the daily doses comprises at least 163 µg of IGF-2 or the variant thereof per kg of the weight of the subject. In some instances, each of the daily doses comprises at least 244 µg of IGF-2 or the variant thereof per kg of the weight of the subject. In some instances, each of the daily doses comprises at least 813 µg of IGF-2 or the variant thereof per kg of the weight of the subject. In some instances, each of the daily doses comprises 163-1626 µg of IGF-2 or the variant thereof per kg of the weight of the subject.

Further aspects provide methods of treating diabetes by administering IGF-2 or a variant thereof to a subject in need of treatment in an amount from about 65 µg/kg of a weight of the subject to about 1626 µg per kg of the weight of the subject.

In some instances, the administering is repeated on at least 5 days. In some instances, the administering is repeated on at least 10 days. In some instances, the administering in a human can be repeated more frequently that in an animal, such as a mouse. In some instances, a subject can receive a daily dose of IGF-2 or the variant thereof divided among one, two, three, or more injections (or another route of administration) in order to achieve a particular daily dose (e.g., at least 800 (HED of 65), 3000 (HED of 244) (referred to in the Figures as 1X1 or X1), 12,000 (HED of 976) (referred to in the Figures as 1X4 or X4) µg per kg of weight of the subject). The subject can receive a daily dose of IGF-2 or the variant thereof on consecutive days (e.g., at least 5, at least 10, at least 15, at least 20, at least 25, at least 30, at least 40, or at least 50 consecutive days). The IGF-2 or the variant thereof can be provided to a subject by any suitable route of administration (orally, injection, subcutaneously, transdermal, etc.).

Further aspects provide methods of lowering the blood level of glucose in a subject by administering IGF-2 or a variant thereof to a subject in need of treatment in an amount from about 65 µg/kg of a weight of the subject to about 813 µg per kg of the weight of the subject.

In some instances, the blood level of glucose is lowered to about normal levels compared to a subject that does not receive the IGF-2 or a variant thereof.

In some instances, the administering is repeated on at least 5 days. In some instances, the administering is repeated on at least 10 days. In some instances, the administering is repeated on at least 15 days. In some instances, the administering is repeated on at least 20 days.

Further aspects provide pharmaceutical compositions comprising IGF-2 or a variant thereof in an amount sufficient to lower the blood glucose level of a subject to about normal levels compared to a subject that does not receive the IGF-2 or a variant thereof, and a pharmaceutically acceptable excipient.

In some instances, the amount of IGF-2 or a variant thereof is from about 3.25 mg to about 49 mg. In some instances, the amount of IGF-2 or variant thereof is from about 8.13 mg to about 41 mg. In some instances, the amount of IGF-2 or variant thereof is from about 24 mg to about 33 mg.

In some instances, the pharmaceutical composition is administered to a subject who exhibits abnormal insulin resistance, abnormal blood glucose level, abnormal insulin level, abnormal glycosylated hemoglobin level, or a combination thereof.

In some instances, the IGF-2 is human IGF-2 or a variant thereof. Optionally, the human IGF-2 is recombinant.

In some instances, the pharmaceutical composition can be administered to the subject at least once a day on at least 5 days. In some instances, the pharmaceutical composition can be administered to the subject at least once per day on at least 8 days. In some instances, the pharmaceutical composition can be administered to the subject at least once per day on at least 10 days.

In an aspect, IGF-2 can be used in a composition to treat a patient in need thereof, wherein the patient has diabetes or type 2 diabetes in accordance with the compositions and methods described herein.

Aspects described herein provide methods of treating type 2 diabetes in a subject in need of treatment and having a weight. The method comprises administering first, second, third, fourth, and fifth daily doses of IGF-2 or a variant thereof to the subject on respective days, wherein each of the daily doses comprises at least 244 µg of IGF-2 or the variant thereof per kg of the weight.

In some instances, each of the daily doses comprises at least 976 µg of IGF-2 or the variant thereof per kg of the weight. In some instances, the subject is treated with IGF-2 or a variant thereof for at least a 35 day course of treatment and a concentration of glucose in a bloodstream of the subject measured after a 14 hour fast does not exceed 200 mg/dl measured after the 35 day course of treatment and after the 14 hour fast.

Aspects described herein provide methods of preventing an onset of type 1 diabetes in a subject having a weight. The method comprises administering first, second, third, fourth, and fifth daily doses of IGF-2 or a variant thereof to the subject on respective days, wherein each of the daily doses comprises at least 65 µg of IGF-2 or a variant thereof per kg of the weight.

In some instances, each of the daily doses comprises at least 976 µg of IGF-2 or a variant thereof per kg of the weight. In these instances, the concentration of glucose in the blood of the subject is less than 300 mg/dl within at least 180 minutes after the subject receives a glucose dose of 2 grams per kg of weight of the subject measured after the fifth daily dose and the at least 180 minutes.

Further aspects described herein provide methods of increasing insulin levels in a bloodstream of a subject having diabetes and having a weight. The method comprises administering first, second, third, fourth, and fifth daily doses of IGF-2 or a variant thereof to the subject on respective days, wherein each of the daily doses comprises at least 65 µg of IGF-2 or a variant thereof per kg of the weight.

In some instances, a concentration of insulin in the bloodstream of the subject is increased by at least 50% compared to an initial concentration of insulin in the bloodstream of the subject measured prior to administration of IGF-2 or a variant thereof to the subject.

In some instances, each of the daily doses comprises at least 244 µg of IGF-2 or the variant thereof per kg of the weight. In some instances, each of the daily doses comprises at least 976 µg of IGF-2 or the variant thereof per kg of the weight.

Aspects described herein provide methods of increasing a number of functional beta cells in a subject having diabetes and having a weight. The method comprises administering first, second, third, fourth, and fifth daily doses of IGF-2 or a variant thereof to the subject on respective days, wherein each of the daily doses comprises at least 65 µg of IGF-2 or a variant thereof per kg of the weight.

In some instances, the number of functional beta cells in the subject is increased by at least four fold after at least 70 days of administering the IGF-2 or the variant thereof to the subject compared to an initial number of functional beta cells in the subject measured prior to administration of IGF-2 or a variant thereof to the subject.

In some instances, each of the daily doses comprises at least 244 µg of IGF-2 or the variant thereof per kg of the weight. In some instances, each of the daily doses comprises at least 976 µg of IGF-2 or the variant thereof per kg of the weight.

Yet further aspects described herein provide methods of preventing an onset of type 2 diabetes in a subject having a weight. The method comprises administering first, second, third, fourth, and fifth daily doses of IGF-2 or a variant thereof to the subject on respective days, wherein each of the daily doses comprises at least 65 µg of IGF-2 or a variant thereof per kg of the weight.

Methods and compositions described herein may further comprise reducing at least one of insulin resistance, blood glucose level, obesity, hyperinsulinemia, glycosylated hemoglobin level, or a combination thereof in the subject.

IGF-2 includes SEQ ID NO: 1 and variants thereof including, but not limited to, human IGF-2 and recombinant IGF-2.

| SEQ ID NO: | Human Accession | Gene Name |
|---|---|---|
| 1 | P01344 | IGF2 |

The active components described for use herein can be included in a pharmaceutically suitable vehicle, selected to render such compositions amenable to delivery by oral, rectal, parenteral (e.g., intravenous, intramuscular, intraarterial, intraperitoneal, and the like), or inhalation routes, osmotic pump, and the like.

Pharmaceutical compositions contemplated for use in the practice of the present invention can be used in the form of a solid, a solution, an emulsion, a dispersion, a micelle, a liposome, and the like, wherein the resulting composition contains one or more of the active compounds contemplated for use herein, as active ingredients thereof, in admixture with an organic or inorganic carrier or excipient suitable for nasal, enteral or parenteral applications. The active ingredients may be compounded, for example, with the usual non-toxic, pharmaceutically and physiologically acceptable carriers for tablets, pellets, capsules, troches, lozenges, aqueous or oily suspensions, dispersible powders or granules, suppositories, solutions, emulsions, suspensions, hard or soft capsules, caplets or syrups or elixirs and any other form suitable for use. The carriers that can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening and coloring agents may be used. The active compounds contemplated for use herein are included in the pharmaceutical composition in an amount sufficient to produce the desired effect upon the target process, condition or disease.

In addition, such compositions may contain one or more agents selected from flavoring agents (such as peppermint, oil of wintergreen or cherry), coloring agents, preserving agents, and the like, to provide pharmaceutically elegant and palatable preparations. Tablets containing the active ingredients in admixture with non-toxic pharmaceutically acceptable excipients may also be manufactured by known methods. The excipients used may be, for example, (1) inert diluents, such as calcium carbonate, lactose, calcium phosphate, sodium phosphate, and the like; (2) granulating and disintegrating agents, such as corn starch, potato starch, alginic acid, and the like; (3) binding agents, such as gum tragacanth, corn starch, gelatin, acacia, and the like; and (4) lubricating agents, such as magnesium stearate, stearic acid, talc, and the like. The tablets may be uncoated, or they may be coated by known techniques to delay disintegration and absorption in the gastrointestinal tract, thereby providing sustained action over a longer period. For example, a time delay material such as glyceryl monostearate or glyceryl distearate may be employed. The tablets may also be coated by the techniques described in U.S. Pat. Nos. 4,256,108; 4,160,452; and 4,265,874, each of which is incorporated herein by reference, to form osmotic therapeutic tablets for controlled release.

When formulations for oral use are in the form of hard gelatin capsules, the active ingredients may be mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, olive oil and the like.

The pharmaceutical compositions may be in the form of a sterile injectable suspension. Such a suspension may be formulated according to known methods using suitable dispersing or wetting agents and suspending agents. The sterile injectable preparation may also be a sterile injectable solution or suspension in a non-toxic parenterally-acceptable excipient, diluent, or solvent, for example, as a solution in 1,4-butanediol. Sterile, fixed oils are conventionally employed as a solvent or suspending medium. For this purpose, any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

In addition, sustained release systems, including semipermeable polymer matrices in the form of shaped articles (e.g., films or microcapsules) can also be used for the administration of the active compound employed herein.

Isolated Nucleic Acid Molecules, and Variants and Fragments Thereof

In an aspect, the disclosure provides for isolated or recombinant nucleic acid molecules comprising nucleotide sequences encoding proteins described herein, for example, SEQ ID NO: 1. In another aspect, the disclosure provides for isolated or recombinant nucleic acid molecules comprising nucleotide sequences encoding proteins described herein, for example, SEQ ID NO: 1.

In an aspect, proteins of the present invention are encoded by a nucleotide sequence. In an aspect, the disclosure provides for a nucleotide sequence encoding an amino acid sequence that has at least 95%, at least 96%, at least 97%, at least 98%, at least 99% or greater sequence identity to a nucleotide sequence encoding SEQ ID NO: 1.

The skilled artisan will further appreciate that changes can be introduced by mutation of the nucleotide sequences of the invention thereby leading to changes in the amino acid sequence of the encoded proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a protein described herein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related sequences of the invention (e.g., residues that have only conservative substitutions between all proteins contained in the alignment homologous proteins). However, one of skill in the art would understand that functional variants may have minor conserved or nonconserved alterations in the conserved residues.

Isolated Proteins and Variants and Fragments Thereof

"Fragments" or "biologically active portions" include protein fragments comprising amino acid sequences sufficiently identical to the amino acid sequence set forth in SEQ ID NO:1, and that exhibit, for example, anti-diabetic activity.

"Variants" means proteins having an amino acid sequence that is at least 95% identical to the amino acid sequence of SEQ ID NO: 1. Variants include proteins that differ in amino acid sequence due to mutagenesis. Variant proteins encompassed by the present invention are biologically active, that is they continue to possess the desired biological activity of the native protein, that is, retaining anti diabetic activity.

In various embodiments of the present invention, anti-diabetic proteins include amino acid sequences that are shorter than the full-length sequences due to the use of an alternate downstream start site.

Altered or Improved Variants

It is recognized that DNA sequences of a protein may be altered by various methods, and that these alterations may result in DNA sequences encoding proteins with amino acid sequences different than in SEQ ID NO:1. This protein may be altered in various ways including amino acid substitutions, deletions, truncations, and insertions of one or more amino acids of SEQ ID NO:1, including up to 2, 3, 4, 5, 6, 7, 8, 9, 10, 15, 20, 25, 30, 35, 40, 45, 50, 55, 60, 65, 70, 75, 80, 85, 90, 100, 105, 110, 115, 120, 125, 130, 135, 140, 145, 150, 155, or more amino acid substitutions, deletions or insertions. Methods for such manipulations are generally known in the art. For example, amino acid sequence variants of a protein can be prepared by mutations in the DNA. This may also be accomplished by one of several forms of mutagenesis and/or in directed evolution. The changes encoded in the amino acid sequence should not substantially affect the function of the protein. Such variants will possess the desired anti-diabetic activity.

Alternatively, alterations may be made to the protein sequence of many proteins at the amino or carboxy terminus without substantially affecting activity. This can include insertions, deletions, or alterations introduced by modem molecular methods, such as PCR, including PCR amplifications that alter or extend the protein coding sequence by inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Theory of Operation

In healthy subjects, insulin regulates glucose uptake. But in diabetic subjects, insulin no longer performs that role effectively (due to either inadequate levels of insulin or insulin resistance). It has been determined that IGF-2 can be used to resolve type II diabetes.

While not wishing to be bound by theory, the following is one possible explanation of the mechanism of action of the disclosed invention. The inventor theorizes that certain cells in the body, referred to herein as "BLC" (which stands for beta-like cells) can be induced to secrete either insulin or an insulin-like material ("ILM") in response to high levels of glucose. Note that while the location of the BLC within the body has not yet been identified, knowledge of their location is not necessary to obtain the results described herein. It is also possible that new BLC may be generated, for example, by proliferation or transdifferentiation, or the like.

More specifically, before the BLC are exposed to IGF-2, the BLC are dormant or inactivated, in which case they do not secrete insulin or ILM or secrete an insufficient amount of insulin or ILM. But after exposure to IGF-2, the BLC become activated, and will begin to secrete insulin or ILM in response to high levels of glucose. One possible mechanism of action is that exposure to IGF-2 causes the BLC to secrete insulin and/or ILM in response to high levels of glucose. Another possible mechanism of action is that the BLC are naturally programmed to secrete insulin and/or ILM in response to high levels of glucose, but an unknown substance that deactivates the BLC is ordinarily present. Under this scenario, IGF-2 neutralizes (e.g., switches off) this normally prevailing deactivation substance.

In either scenario, once the BLC have been activated, the BLC will sense the level of glucose in the blood, and will initiate the production of insulin or ILM at levels that correspond to the level of glucose in the blood (so that higher levels of glucose will result in the production of more insulin or ILM). This production of insulin or ILM may occur either directly in the BLC themselves or indirectly (e.g., through the action of other cells). The insulin or ILM circulates in the blood.

Another possible explanation of the mechanism of action is that exposure to IGF-2 improves conventional beta cells' ability to regulate the glucose levels in a subject's body, or downregulates/turns off another mechanism that prevents the conventional beta cells from properly regulating glucose levels. To the extent this theory is correct, it is believed that treatment with IGF-2 as disclosed herein may restore the normal activity of residual beta cells.

EXAMPLES

Example 1—Materials and Methods

C57BU/6 mice male 8-10 weeks old, housed under conventional conditions and allowed laboratory chow and water ad libitum, were used in the experiments described below in Examples 3-4. Within each experiment, animals were matched by age and weight (20-24 g) and randomly divided into groups to receive different treatments. Diabetes was induced by one or more doses of streptozotocin (STZ).

Briefly, animals received intraperitoneally (i.p.) 100 mg/kg (b.w.) STZ (Cayman Chemical, Ann Arbor, MI) dissolved in citrate buffer on pH 4.5 (this procedure was repeated if needed). Clinical diabetes was defined by hyperglycemia (blood glucose levels >300 mg/dL in fasted animals). Fasting blood glucose levels were measured three times per week and samples were taken from the tail tip after starvation for 6 hours throughout the experiment.

Fasting blood glucose levels (mg/dL) were determined using the Accu-Chek Performa glucometer (Roche Diagnostics, Mannheim, Germany). After approximately two weeks of stable hyperglycemia, C57BL/6 STZ mice received exogenous injections of recombinant human IGF-2 (0.3-12 mg/kg/day injection) intraperitoneally for 5-10 consecutive days. During post-treatment follow-up period and upon termination, mice were tested for fasting glucose, body weight, glucose tolerance test (IPGTT), serum C-peptide level, serum insulin level, and full blood and histological analysis (CBC, Chemistry, Insulin IHC and H&E).

Example 2—IGF-2 3000 Ug/Kg/Day Dose

FIGS. 1-4 show the effects of IGF-2 at 3000 µg/kg/day in four different mice treated in accordance with the description for Example 1.

Mouse C1 (FIG. 1), Mouse C8 (FIG. 2), and Mouse C6 (FIG. 3) received STZ 25 days prior to beginning treatment with IGF-2 and exhibited a roughly four-fold increase in fasting glucose levels. IGF-2 (at 3000 µg/kg/day) was administered on day 0 and ten more times within the first ten days following the initial treatment with IGF-2. Fasting glucose levels returned to a normal range during the ten-day course of treatment with IGF-2, and remained in the normal range until the end of the experiment. Notably, the improvement in fasting glucose levels appeared to be permanent (or at least semi-permanent) because IGF-2 was not administered on days 11-82.

Mouse F1 (FIG. 4) was treated similarly to Mouse C1, Mouse C8 and Mouse C6 except STZ was provided 20 days prior to initial treatment with IGF-2. The fasting glucose results for Mouse F1 was similar to Mouse C1, Mouse C8 and Mouse C6.

While the four examples depicted in FIGS. 1-4 all show long term improvement in fasting glucose levels, in some mice (not shown) the fasting glucose results returned to high levels after the 10 day course treatment with IGF-2 ended.

Example 3—IGF-2 ¼ Dose (800 µg/Kg/Day)

Figure 5A:
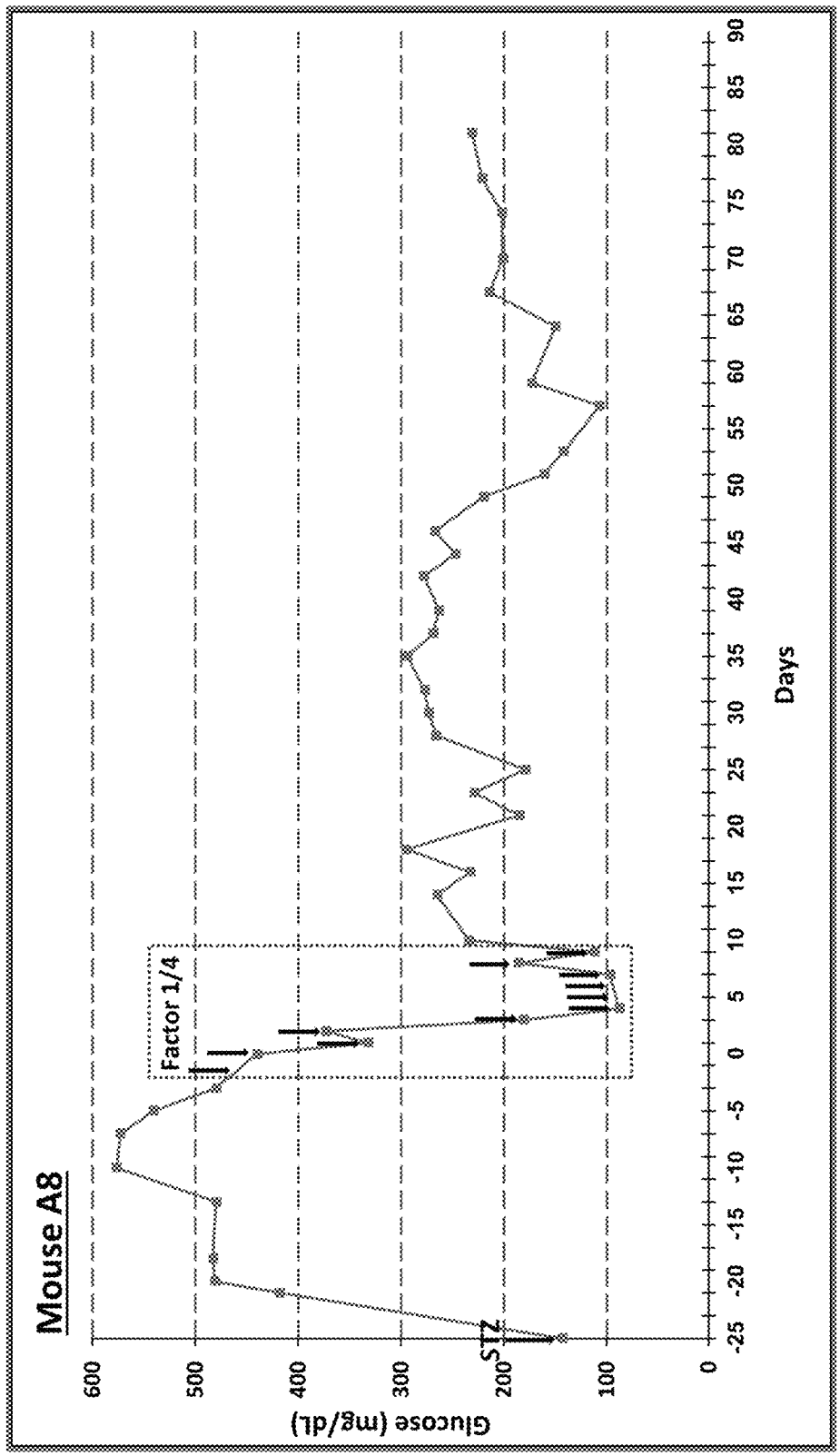
FIGS. 5A, 5B, 6A, and 6B depict the exemplary blood glucose levels in four mice during experiments in which diabetes was induced with STZ and IGF-2 was provided to the mouse at the time points indicated at a daily dose of 800 μg/kg (¼ dose)

Mouse A8 (FIG. 5A) received STZ 25 days prior to beginning treatment with IGF-2, and exhibited a roughly four-fold increase in fasting glucose levels. IGF-2 (at 800 µg/kg/day) was administered on day 0 and ten more times within the first ten days following the initial treatment with IGF-2. Fasting glucose levels returned to a normal range during the ten-day course of treatment with IGF-2, and remained in the normal range until the end of the experiment. The improvement in fasting glucose levels appeared to be permanent or at semi-permanent).

Figure 5B:
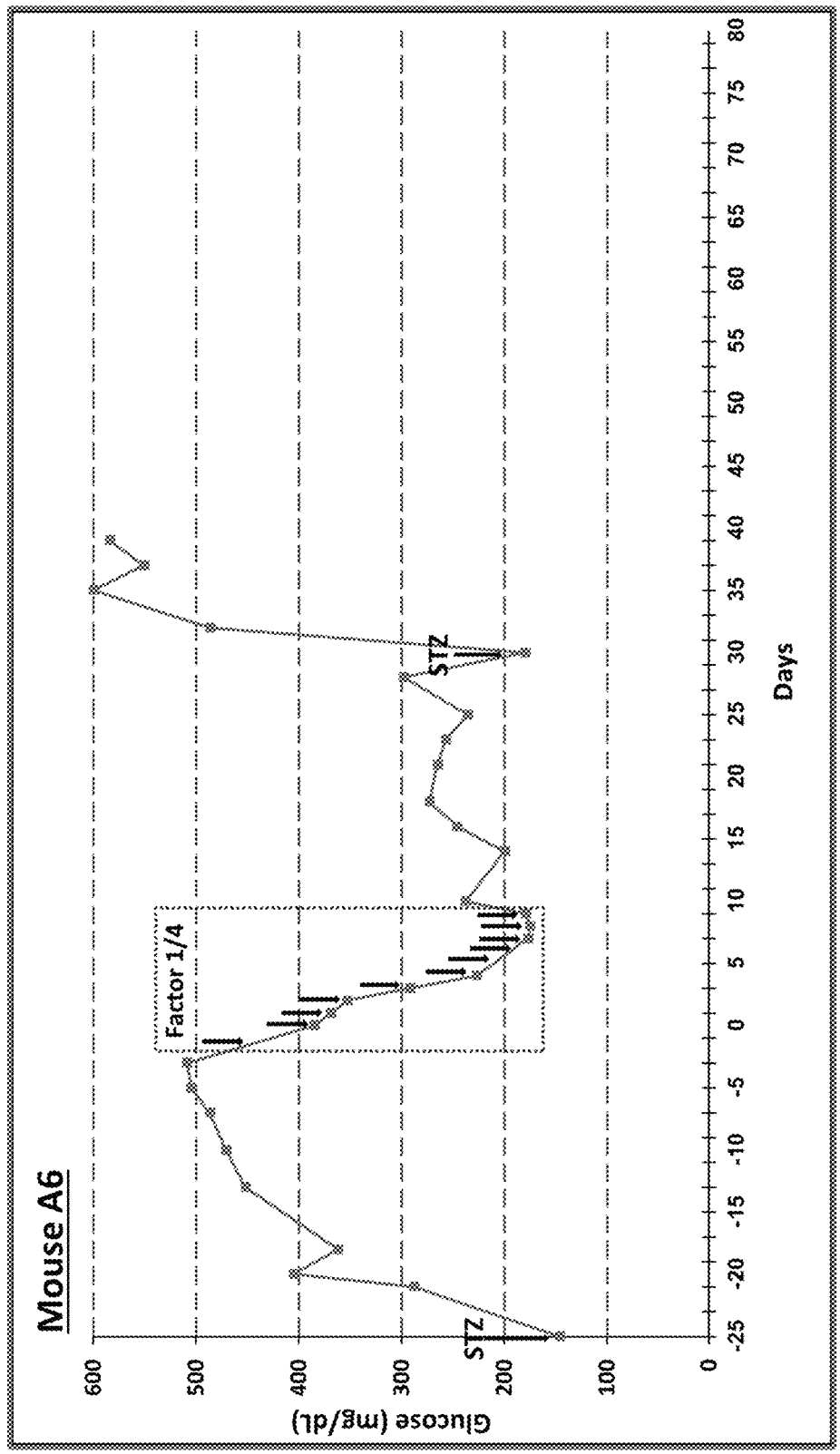

Mouse A6 (FIG. 5B) received STZ 25 days prior to beginning treatment with IGF-2 and exhibited a roughly four-fold increase in fasting glucose levels. IGF-2 (at 800 µg/kg/day) was administered on day 0 and ten more times within the first ten days following the initial treatment with IGF-2. Fasting glucose levels returned to a normal range during the ten-day course of treatment with IGF-2, and remained in the normal range until STZ was provided again. After the second administration of STZ, fasting glucose levels rose back into the diabetic range, indicating that the mechanism responsible for returning the glucose levels to the normal range was susceptible to destruction by STZ.

Figure 6A:
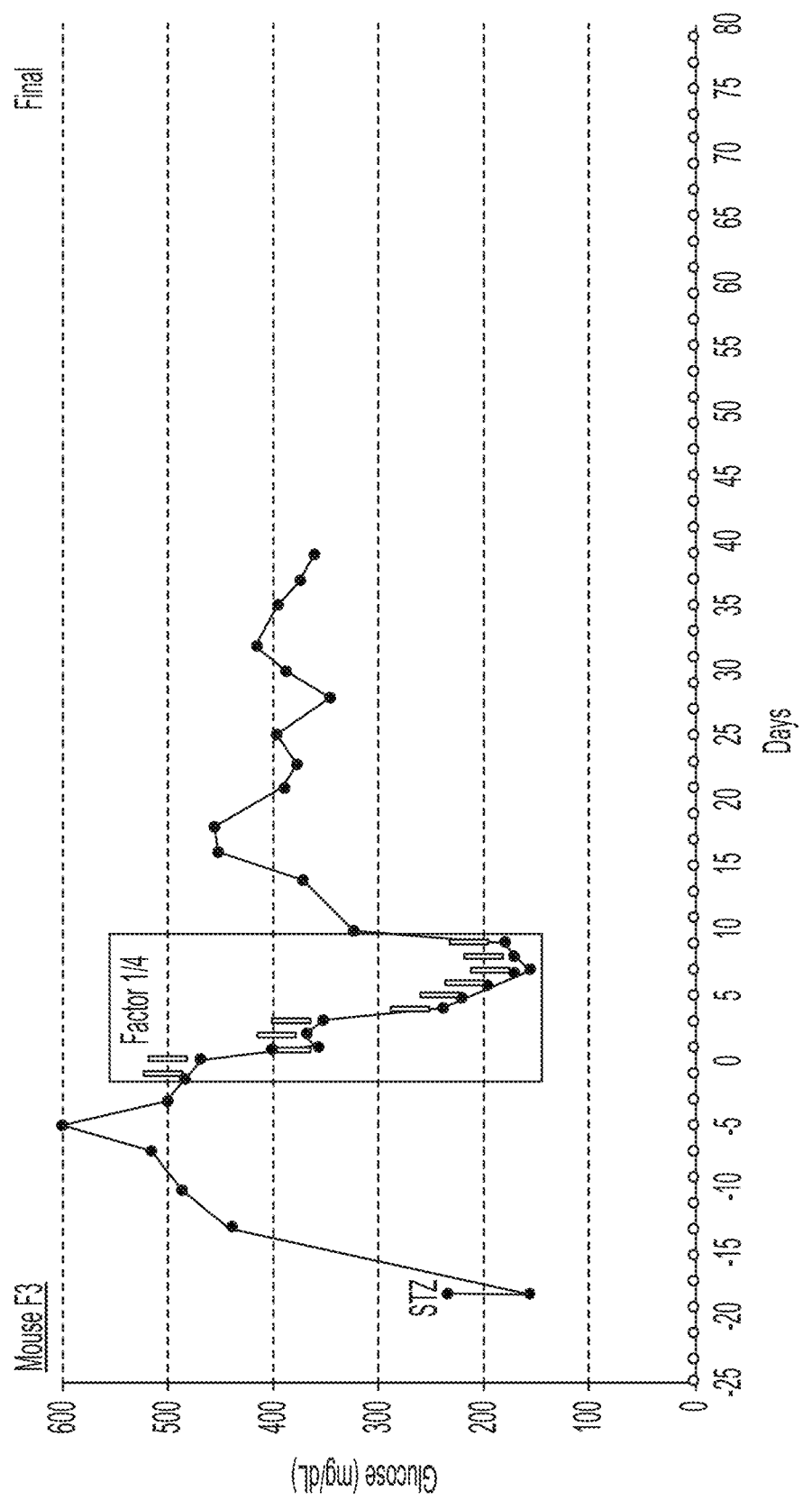
Figure 6B:
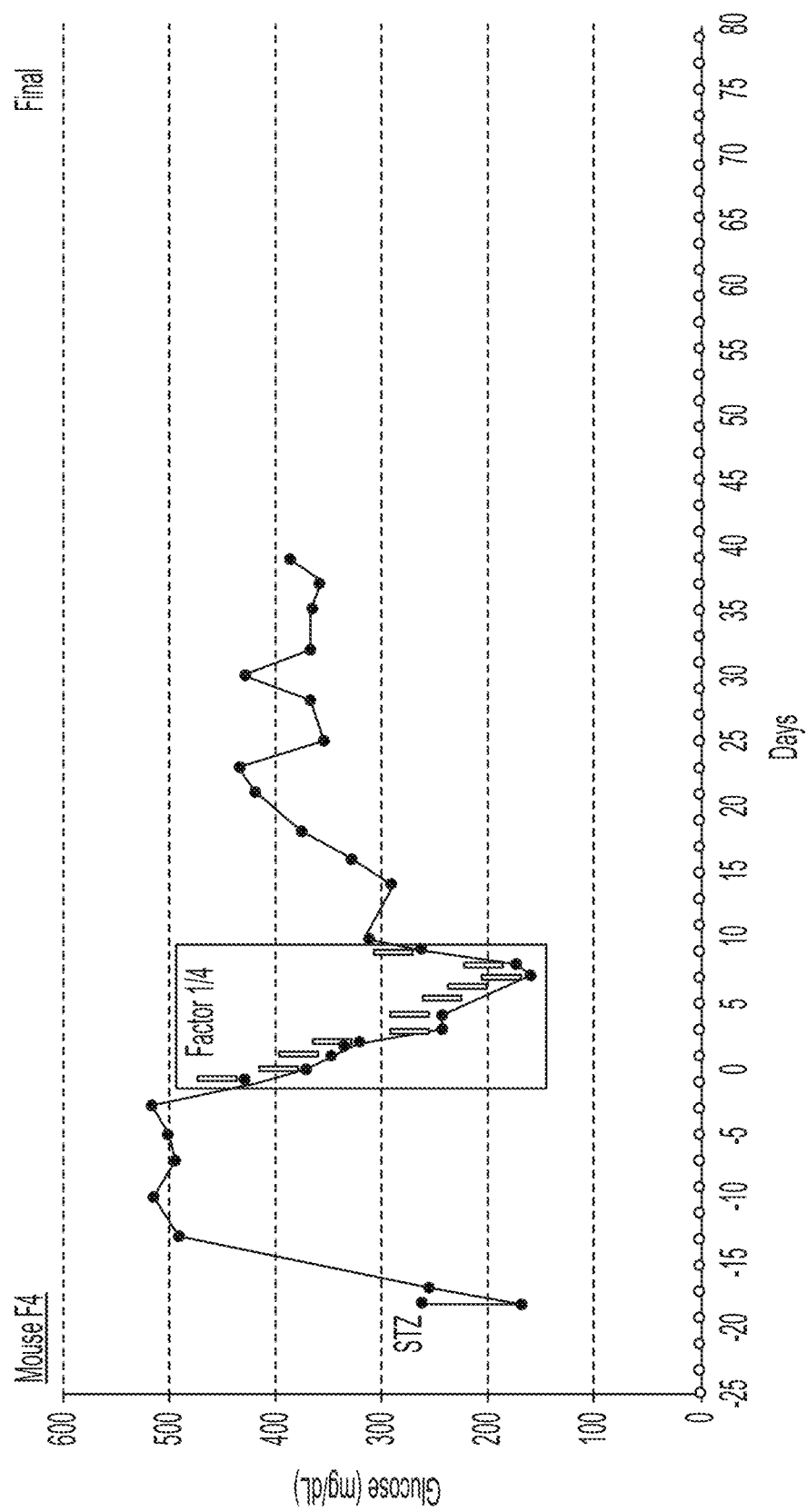

Mice F3 and F4 (FIGS. 6A and 6B) received STZ 20 days prior to beginning treatment with IGF-2 and exhibited a roughly four-fold increase in fasting glucose levels. IGF-2 (at 800 µg/kg/day) was administered on day 0 and ten more times within the first ten days following the initial treatment with IGF-2. Fasting glucose levels returned to a normal range during the ten-day course of treatment with IGF-2, but went back up to around 400 after the ten day course of injections ended. Thus, for these two mice, long-term results were not achieved.

In this example, the results at the 800 µg/kg/day dosage were variable. Half the mice had a full or almost full resolution (i.e., with blood glucose levels remaining in the vicinity of 200 mg/dl as in FIGS. 5A and 5B). The remaining mice had a partial improvement (i.e., with blood glucose levels remaining in the vicinity of 400 mg/dl as in FIGS. 6A and 6B).

Example 4—IGF 300 Ug/Kg/Day Dose

Figure 7:
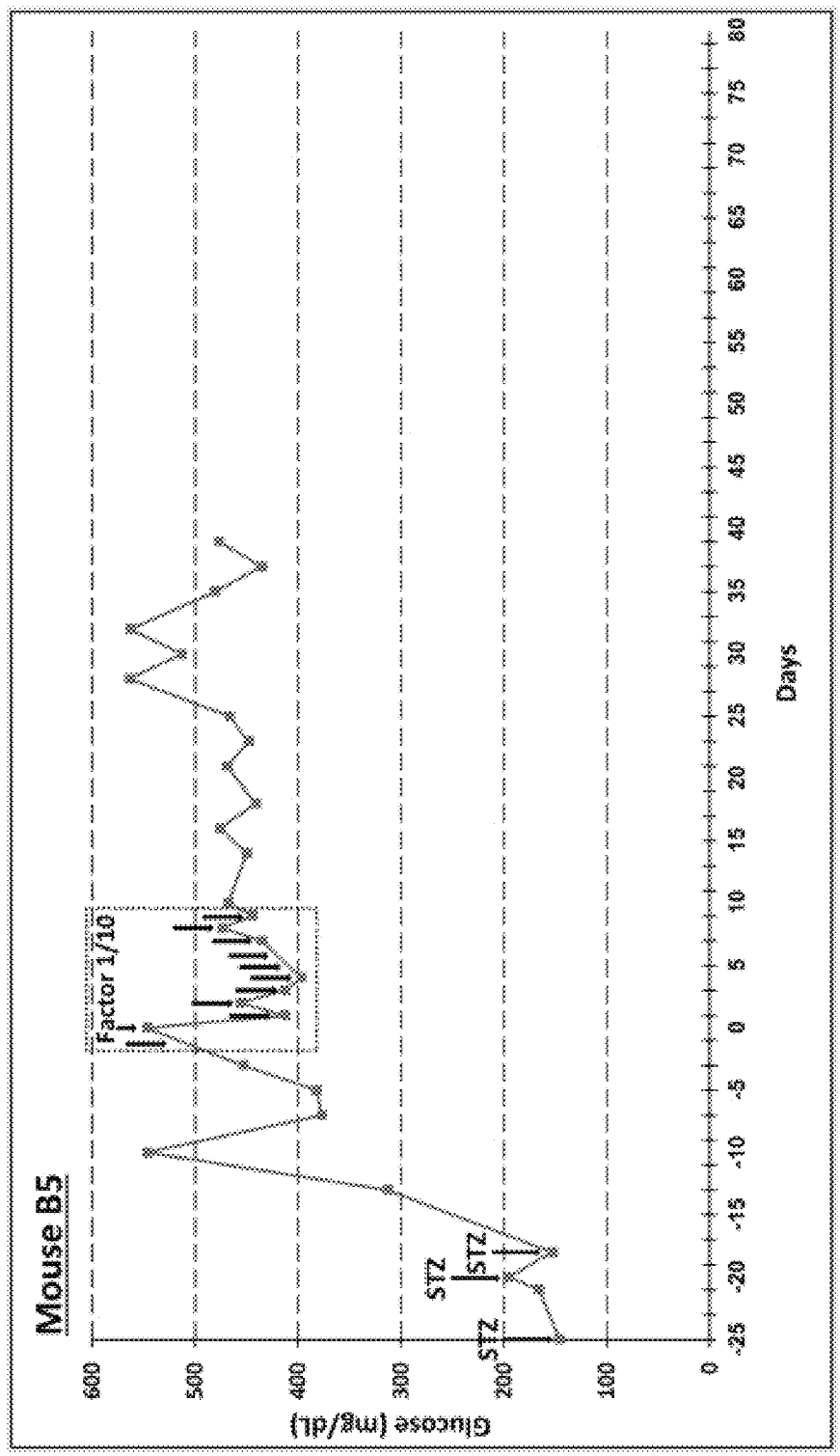
FIGS. 7-10 depict the exemplary blood glucose levels in four mice during experiments in which diabetes was induced with STZ at the indicated time points and IGF-2 was provided to the mouse at the indicated time points at a daily dose of 300 μg/kg (1/10 dose)

Mouse B5 (FIG. 7) was treated with STZ three times (25, 20, and 17 days) prior to an initial 300 µg/kg/day of IGF-2 followed by ten additional 300 µg/kg/day doses of IGF-2 the course of ten days. Unlike the higher-dose situations described above in connection with FIGS. 1-6, the fasting glucose levels did not return to a normal range, and long-term results were not observed.

Figure 8:
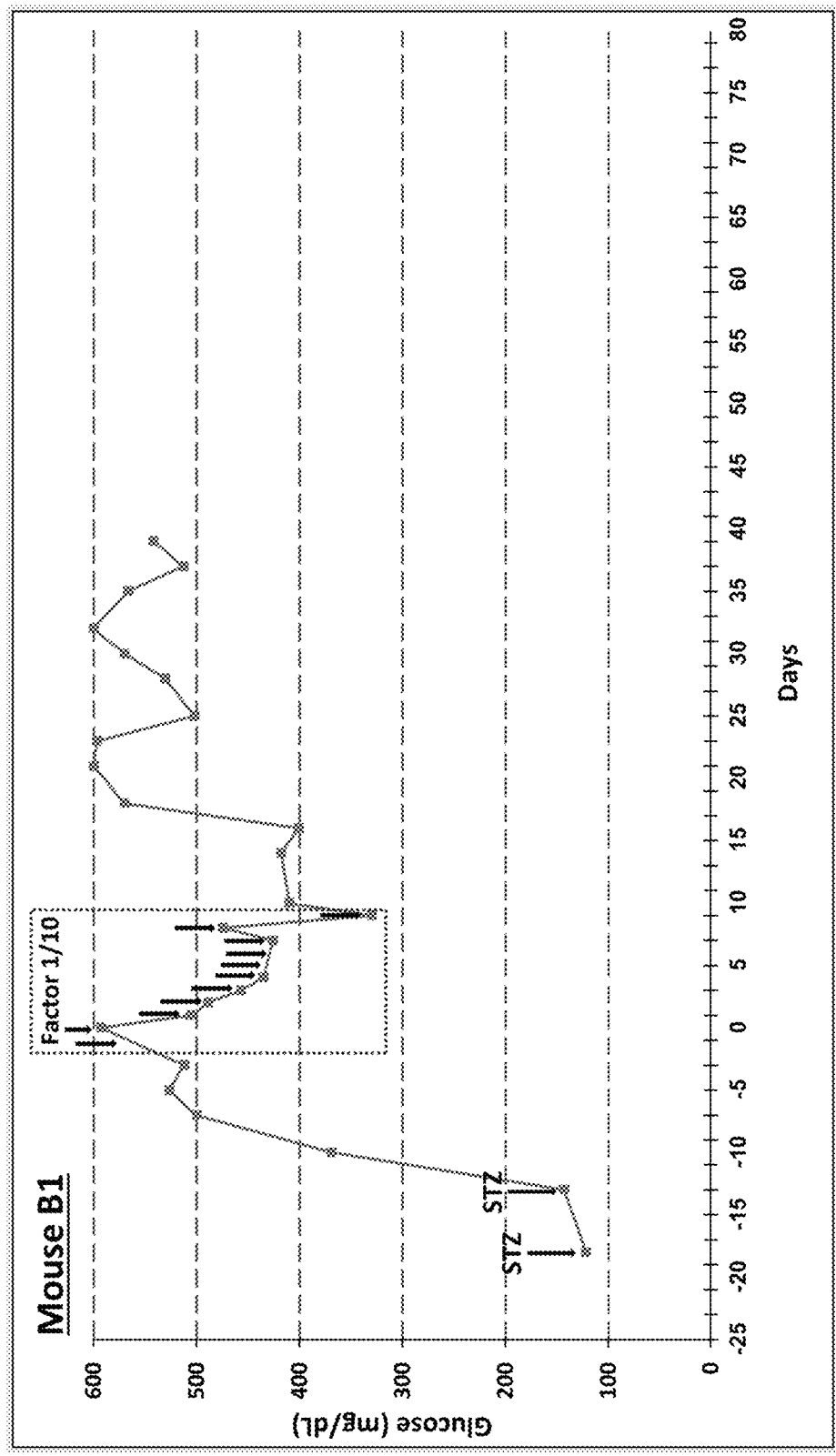

Mouse B6 (FIG. 8) was treated similarly to Mouse B5 except Mouse B6 received two doses of STZ at 20 and 12 days prior to the course of treatment with IGF-2 at a 300 µg/kg/day dose. The results were similar to the results obtained for Mouse B5.

Figure 9:
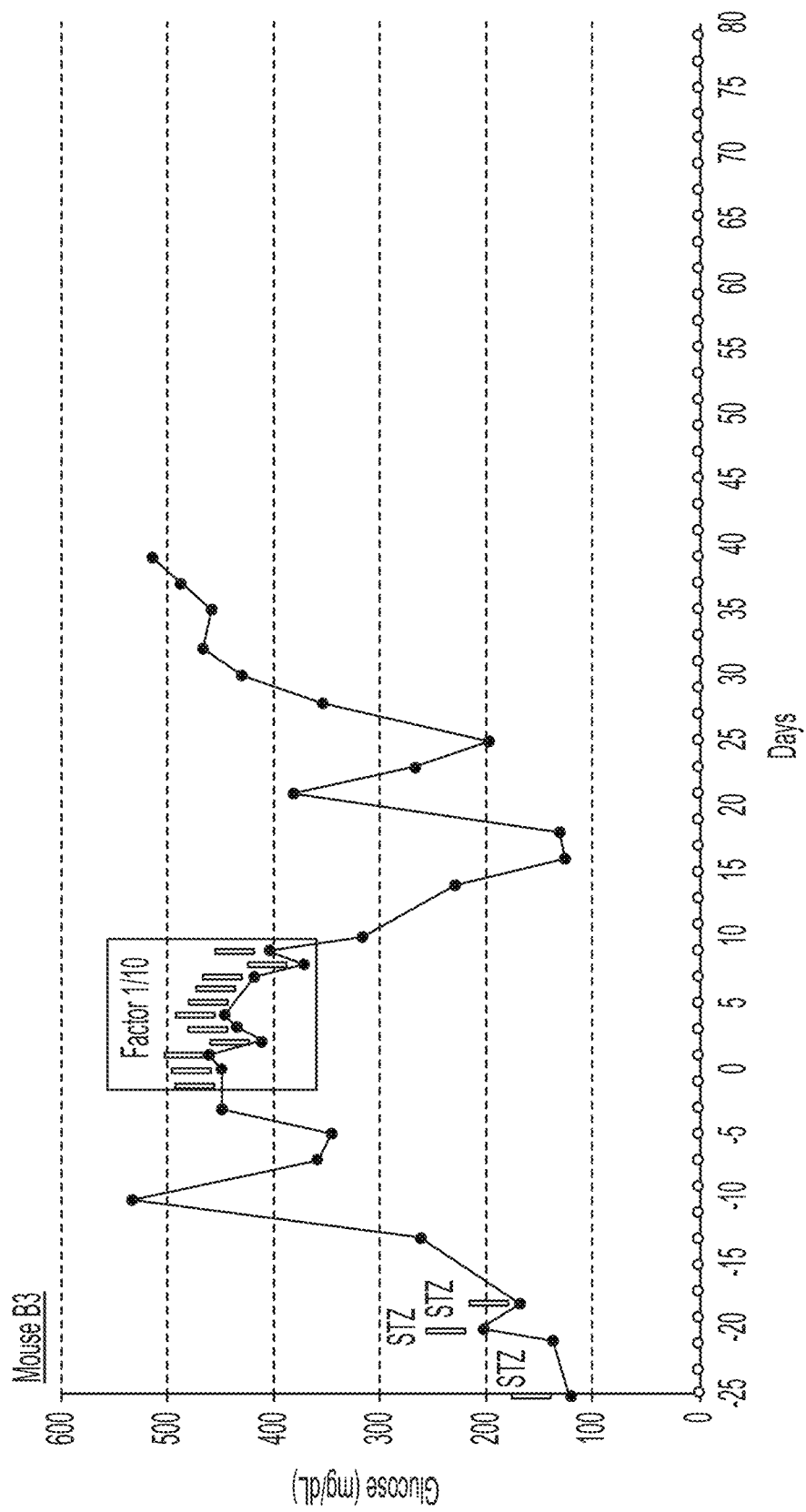

Mouse B3 (FIG. 9) was treated similarly to Mouse B5. Although this mouse did experience a temporary drop in fasting glucose levels from days 10-25, the long-term results were similar to the results for Mouse B5.

Figure 10:
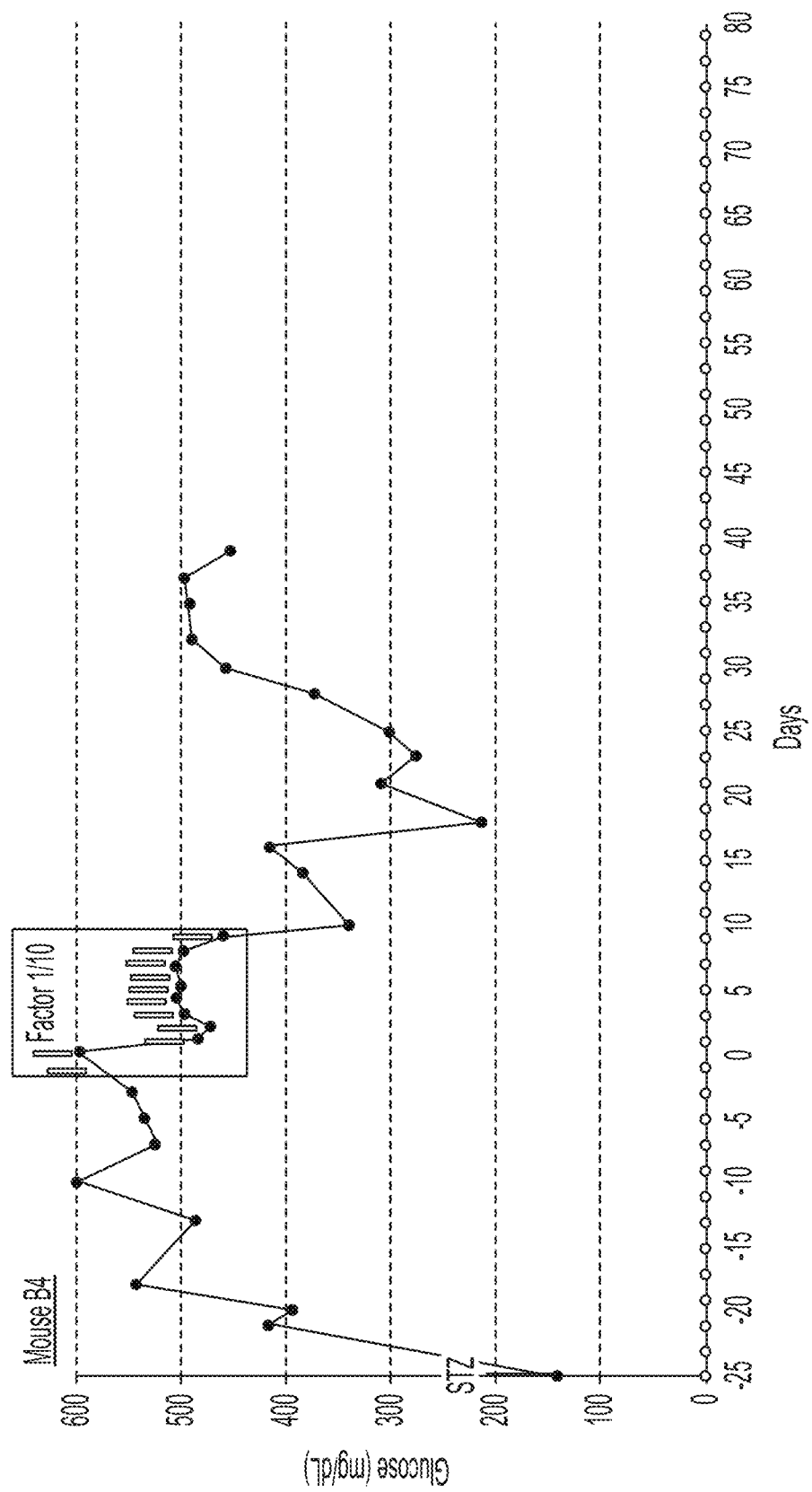

Mouse B4 (FIG. 10) was treated similarly to Mouse B5 except Mouse B6 received a single dose of STZ 25 days prior to the course of treatment with IGF-2 at a 300 µg/kg/day dose. This mouse also experienced a temporary drop in fasting glucose levels from days 10-25, but the long-term results were similar to the results for Mouse B5.

Example 5—Comparison of Repetitions

In some instances, the number of repetitions appears to be a factor in achieving long-term results. FIGS. 11A, 11B, 12A, and 12B depict the exemplary blood glucose levels in four mice during experiments in which diabetes was induced with streptozotocin (STZ) and IGF-2 was provided to the mouse at the time points indicated at a daily dose of 12,000 µg/kg. More specifically, when IGF-2 was provided to the mice on each of 12 consecutive days, long-term improvements in blood glucose levels were obtained (see FIGS. 11A and 11B). But when IGF-2 was provided to the mice on only 5 consecutive days, long-term improvements in blood glucose levels were not obtained (see FIGS. 12A and 12B).

In one aspect, the long-term return of blood glucose to normal levels depends on both the number of repetitions and the IGF-2 dosage of each repetition. A treatment regiment can consider a combination of these two factors. In some instances, when either the number of repetitions or the dosage of each repetition is too small, the glucose levels can eventually return to their elevated values. In some instances, when both the number of repetitions and the dosage in each repetition is large enough, a long-term return of blood glucose to normal levels is achieved (e.g., as described above in connection with FIGS. 1-5 and 11).

Example 6—Pharmacokinetics of IGF-2 (40 µg Intraperitoneal Injection)

Figure 13:
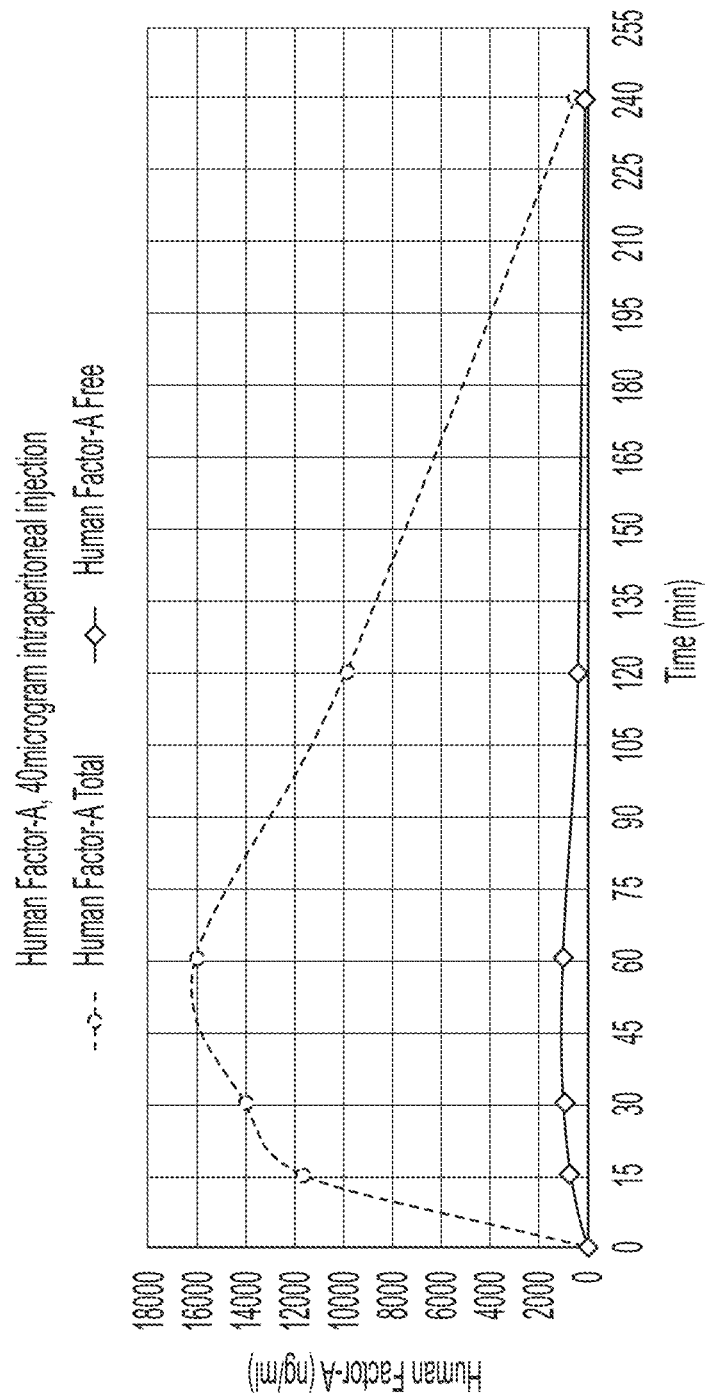
FIG. 13 depicts the exemplary blood concentration of IGF-2 in a mouse over time following an intraperitoneal (IP) injection of 40 μg of IGF-2 (total IGF-2 and free IGF-2)

FIG. 13 shows the level of total IGF-2 (referred to in the figure as "Factor A") in the blood over time following a 40 µg intraperitoneal injection. The results show a peak total concentration of IGF-2 total (about 16 µg) and 1 µg free IGF-2, as determined by ELISA (enzyme-linked immunosorbent assay) over a 240 minute time frame. Without being bound by this theory, it is believed that IGF-2 binding proteins may initially inactivate the biological activity of free IGF-2. And over time, the bond between IGF-2 and the binding protein may be released, increasing the bioavailability of IGF-2 and leading to a longer term effective treatment.

Example 7—Blood Glucose Concentration Kinetics of IGF-2 vs. Insulin

Figure 14:
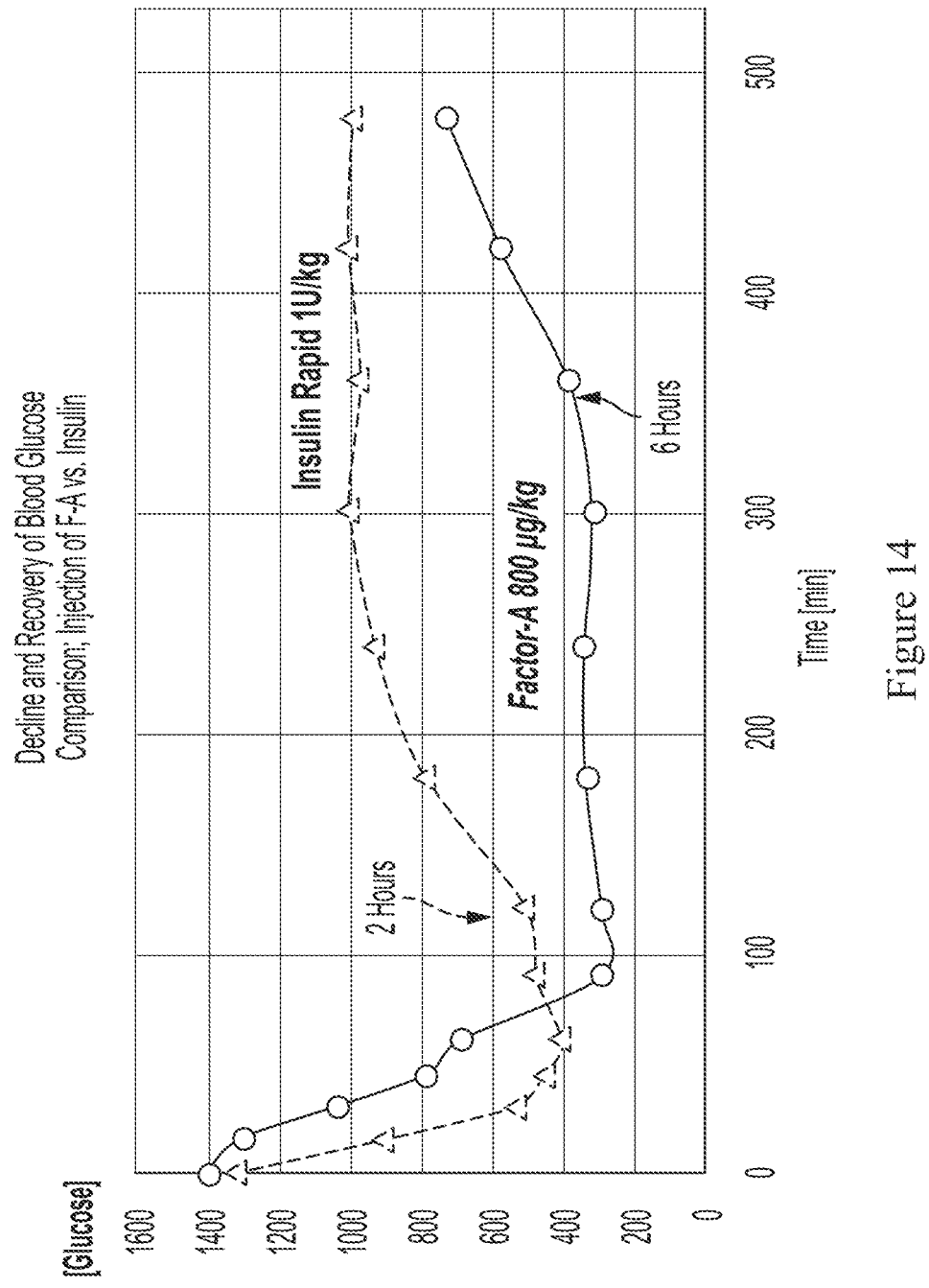
FIG. 14 depicts the exemplary blood glucose levels over time in an experiment comparing the effects of insulin to IGF-2.

FIG. 14 shows the comparative blood glucose concentration kinetics between insulin and IGF-2 (referred to in the figure as "Factor A") in a glucose tolerance test in mice. Notably, after either insulin or IGF-2 was administered, the glucose level decreased. IGF-2 therefore provides an effect that mimics insulin within the body, and that effect is referred to herein as an "insulinomimetic" effect. But notably, as shown in FIG. 14, the insulinomimetic effect of IGF-2 endures for significantly longer than the blood-glucose lowering effects of insulin. More specifically, when 1 unit of insulin per kg was administered, the recovery in glucose levels began after two hours. But when 800 µg/kg of IGF-2 was administered, the recovery in glucose levels began after six hours. Moreover, in the latter case, the glucose levels did not begin to rise until two hours after the IGF-2 was no longer detectable in the blood (see FIG. 13). In this example, administering IGF-2 can provide better results than administering insulin with respect to blood glucose levels, even when only a single dose was used. Without being bound by this theory, it is possible that the IGF-2 combines with a number of binding proteins in the blood and its active free form is then released slowly from the complex.

Example 8—Discussion

Taken together, the data in FIGS. 13 and 14 show that insulinomimetic effects of IGF-2 are separate from the long-term effects of IGF-2 described above in connection with FIGS. 1-5.

The insulinomimetic effect can be used for the treatment of hyperglycemia, while the long-term effect may serve to fully, or partially, cure diabetes long-term. In addition, the blood glucose lowering effect of IGF-2 is not diminished by presence of high "insulin resistance" typical of type 2 diabetes treated with insulin.

Unlike conventional diabetes treatment using insulin (where the dosage must be controlled precisely to prevent hypoglycemia), a very wide range of IGF-2 dosages can be tolerated by living subjects without causing hypoglycemia. More specifically, in the examples above, a 10:1 ratio of dosages (i.e., between 3000 µg and 300 µg) did not cause hypoglycemia. Thus, IGF-2 compositions and methods as described herein can advantageously be used to effectively treat hyperglycemia without the life-threatening risks associated with insulin therapy (e.g., hypoglycemia and insulin resistance). In addition, IGF-2, when used as described herein in connection with FIGS. 1-5, can produce a long-term effect beyond the period of treatment to reduce or even cure diabetes.

Example 9—STZ Treated Mice

FIGS. 15-23 show the results of experiments with mice treated with STZ. STZ eliminates or reduces the secretory capability of pancreatic β cells. STZ-treated mice serve as models of both type 1 diabetes and late stage type 2 diabetes.

Figure 15:
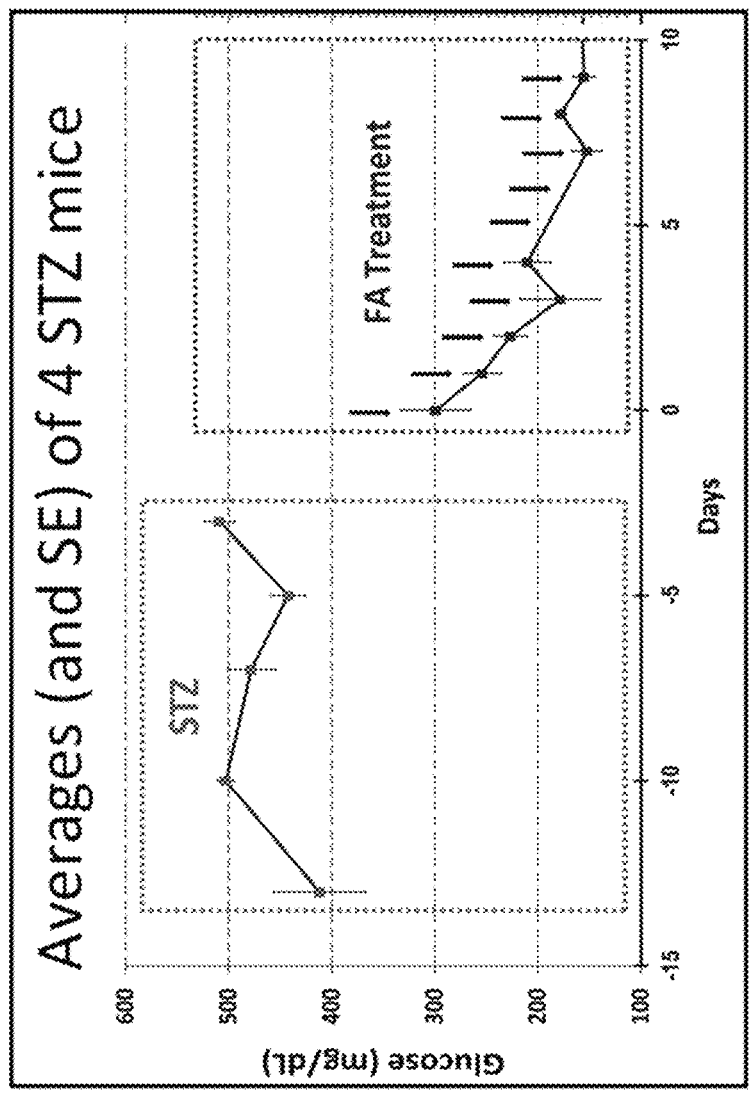
FIG. 15 shows the blood glucose levels averaged over the four STZ-treated mouse experiments depicted in FIGS. 1-4.

FIG. 15 shows the blood glucose levels averaged over the four STZ-treated mouse experiments depicted in FIGS. 1-4 before treatment (left panel) and after treatment (right panel) with the 3000 µg/kg/day dose of IGF-2. As shown in FIG. 15, daily intraperitoneal treatment with the 3000 µg/kg/day of IGF-2 reduced the blood glucose level to a normal range (e.g., 100-200 mg/dL glucose) within 3-5 days and maintained the normal level for the remainder of the 10 day window during which IGF-2 was administered. Hypoglycemia was never observed, even when the IGF-2 dose was increased to 12,000 µg/kg/day.

Figure 16:
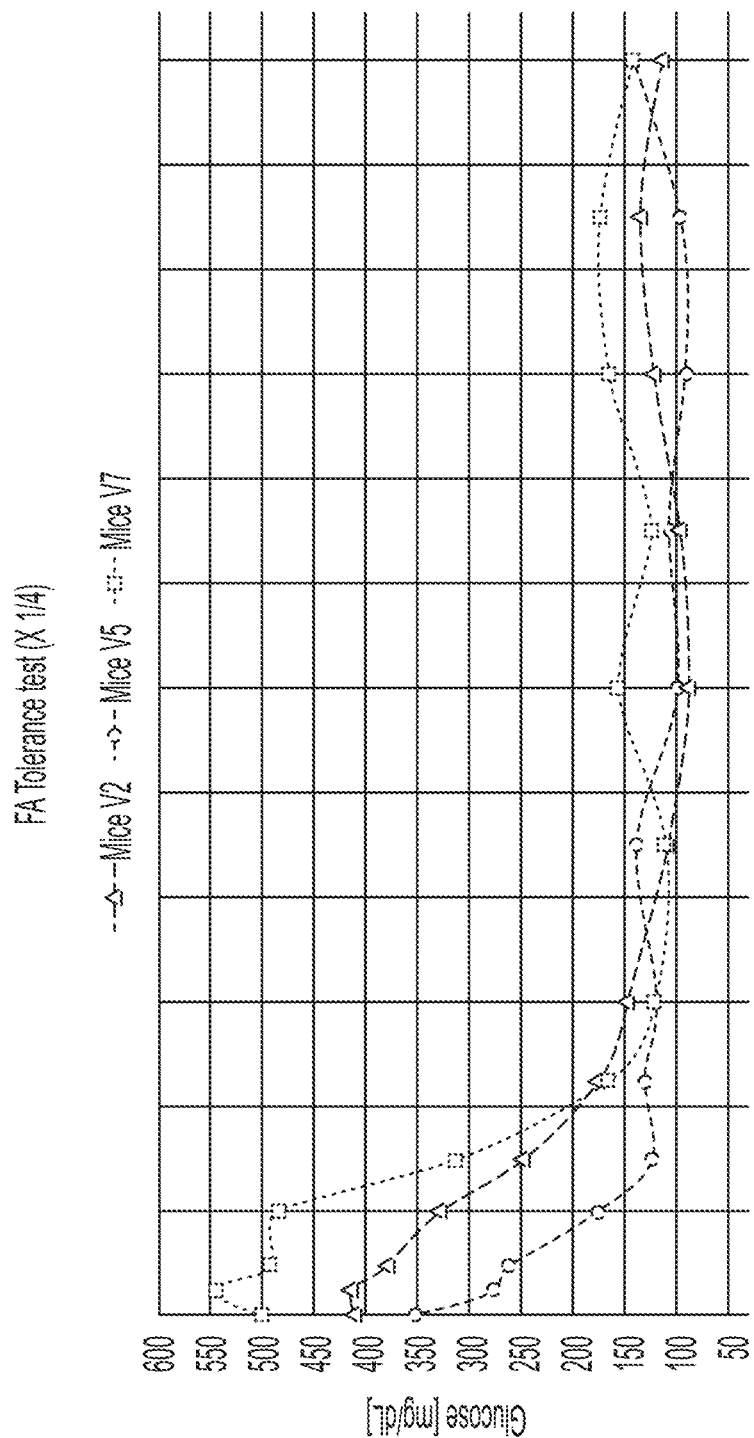
FIG. 16 shows the exemplary short term effects of IGF-2 on glucose levels and IGF-2 levels following injection of IGF-2 in STZ-treated mice.
Figure 16:
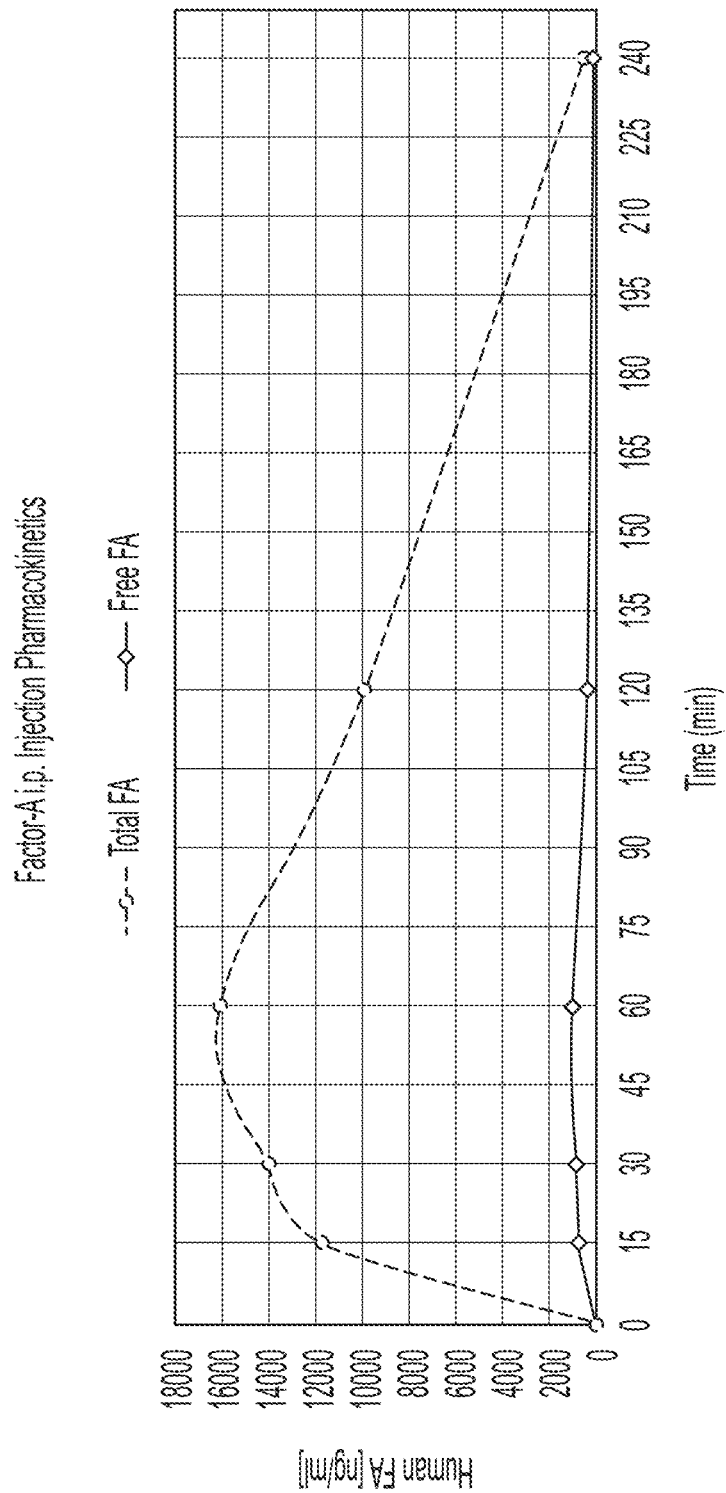

FIG. 16 shows the exemplary short term effects of IGF-2 (referred to in the figure as "Factor A" or FA) on glucose levels and IGF-2 levels over a 240 minute time course following injection of IGF-2 in STZ-treated mice. More specifically, the top panel illustrates the drop in glucose blood levels in three STZ-treated mice after receiving a 800 µg/kg/day dose of IGF-2 over a 240 minute time course. The bottom panel shows the rise in total IGF-2 (upper trace) over the same time course compared to free IGF-2 (i.e., uncomplexed IGF-2). IGF-2 is part of a complex system comprising IGF-1 and IGF-2 along with binding proteins, proteases and other interacting molecules. A single 800 µg/kg dose of IGF-2 injected intraperitoneally lowers hyperglycemic blood glucose levels of 300-500 mg/dL to a normal level (100-200 mg/dL) for periods of over four hours. Normoglycemia is maintained while total serum IGF-2 is reduced to very low levels. Free IGF-2 levels are a small fraction of the total IGF-2 concentration over the time course of the experiment. Without being bound by this theory, it is believed that a slow release of IGF-2 from a serum complex can maintain normal blood glucose levels.

Figure 17:
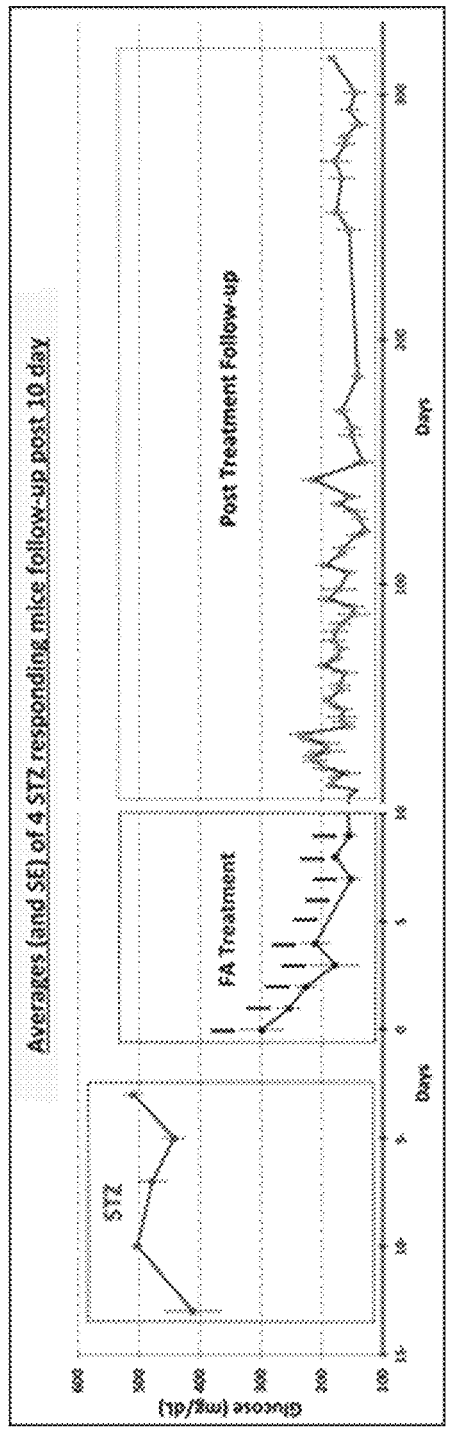
FIG. 17 shows the exemplary long term effects of IGF-2 on glucose levels in STZ-treated mice.

FIG. 17 shows the exemplary long term effects of IGF-2 (referred to in the figure as FA) on glucose levels in STZ-treated mice. More specifically, FIG. 17 shows a long term 300 day follow up study of four mice during and following a 10 day course of treatment with IGF-2 at a 3000 µg/kg/day dose. The data shows that even though no additional doses of IGF-2 were administered after the initial 10 day course of treatment, normal blood glucose levels are maintained out to at least 300 days post treatment. It is believed that the four mice were permanently cured of STZ-induced diabetes by a single 10 day course of treatment.

Figure 18:
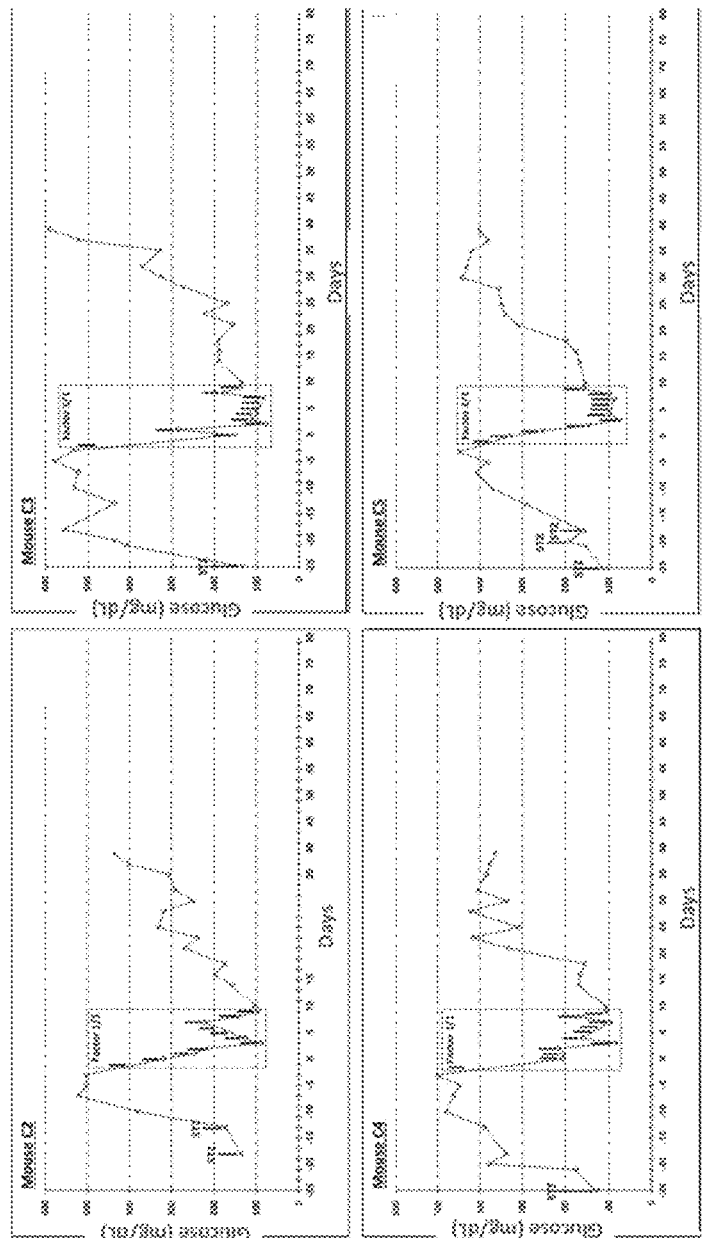
FIG. 18 shows glucose levels in four mice that did not exhibit a permanent response to treatment with IGF-2.

In contrast to the results depicted in FIG. 17, FIG. 18 depicts experimental results for four STZ-treated mice who received a 10 day course of treatment with IGF-2 at a 3000 µg/kg/day dose. These mice initially responded to treatment with a 3000 µg/kg/day dose of IGF-2 but were not permanently cured. Although data was not collected, it is believed that continued treatment of these mice would have maintained blood glucose levels in the normal range. Thus, mice who are not permanently cured can continue to be treated with IGF-2 or a variant thereof in order to control their diabetes.

Figure 19:
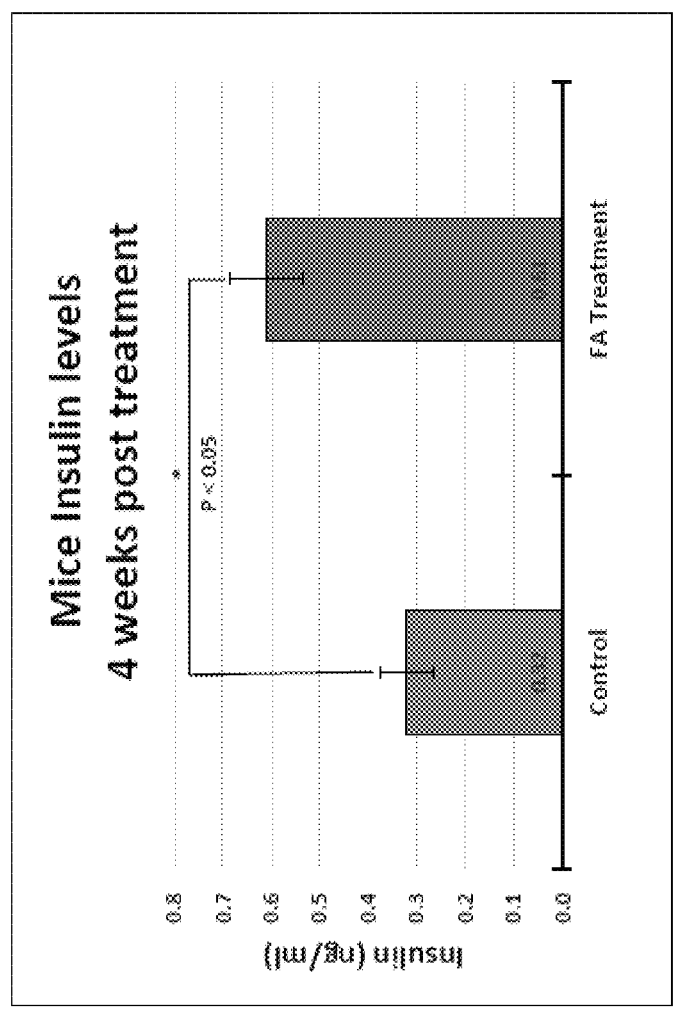
FIG. 19 shows the increase in insulin levels in four STZ-treated mice four weeks after treatment with IGF-2.

FIG. 19 shows the increase in insulin levels four weeks after treatment with IGF-2. The treatment resulted in a significant increase of the insulin concentration post treatment for the permanently cured mice. More specifically, four weeks post treatment, serum insulin was increased by 50% in the permanently cured mice compared to STZ treated control mice which did not receive IGF-2 treatment.

Other experimental data show a 12-fold increase in c-peptide levels of four STZ-treated mice four weeks post treatment as described in FIGS. 18 and 19. C-peptide is a biomarker used to assess pancreatic beta cell function and is normally produced in equimolar amounts to endogenous insulin. Leighton et al., *A Practical Review of C-Peptide Testing in Diabetes, Diabetes Ther.* 2017 June; 8(3): 475-487.

Figure 20:
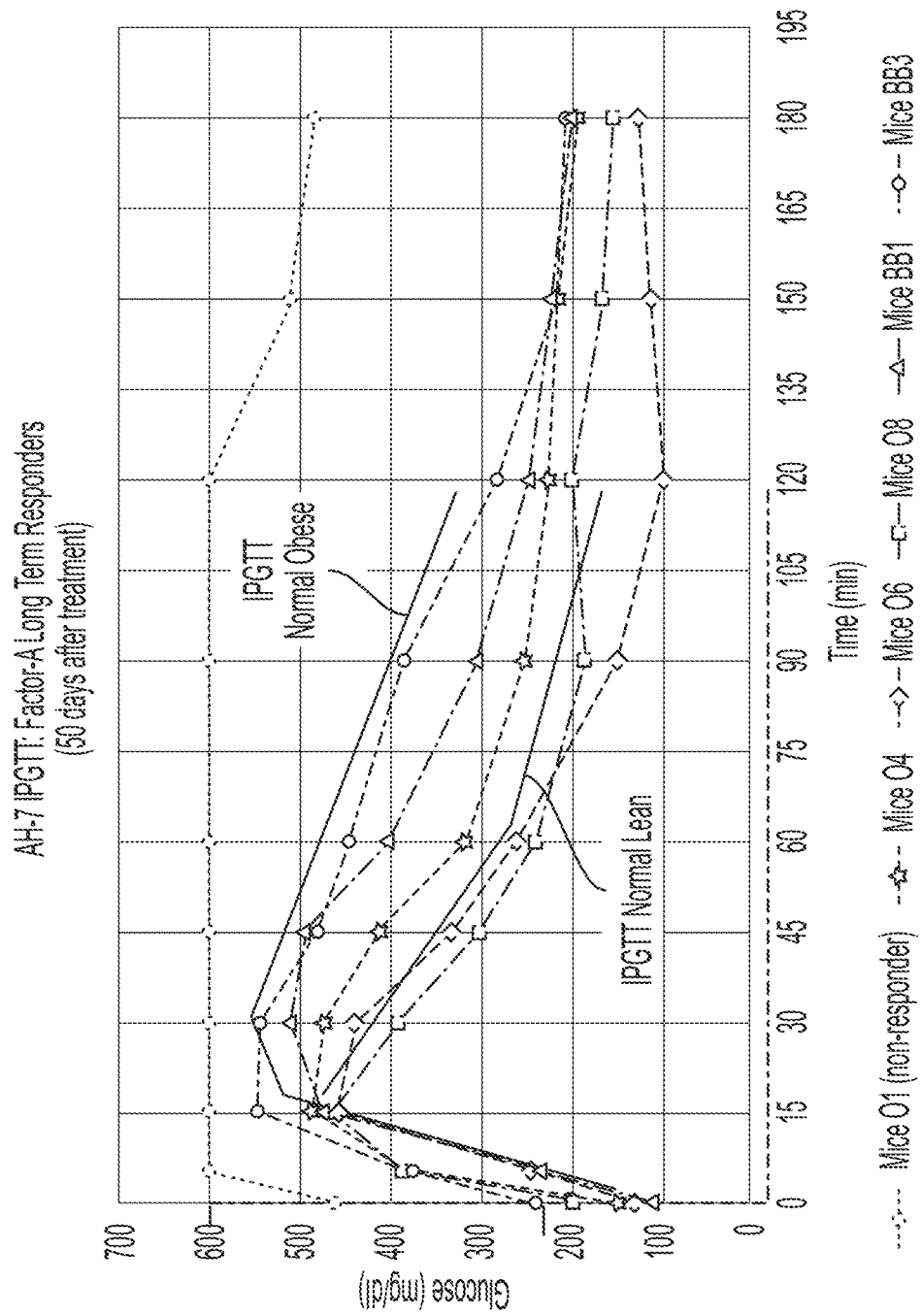
FIG. 20 shows the results of an exemplary glucose tolerance test in STZ-treated mice that were treated with IGF-2.

FIG. 20 shows the results of an intraperitoneal glucose tolerance test on STZ-treated mice that were treated with IGF-2. In this experiment, four STZ-treated mice were treated with 12,000 µg/kg/day of IGF-2 (four injections of 3000 µg/kg/day) 5 days and two mice were treated for 10 days. A glucose tolerance test was performed 50 days post-treatment with IGF-2 by challenging the treated mice with a 2 grams/kg dose of glucose and determining the blood glucose level over a 180 minute time course. The blood glucose curves of the treated mice were compared to results for a saline control, and normal (nondiabetic) obese and normal (nondiabetic) lean mice based on published literature (Jorgensen et al., J. Am Assoc. Lab. Animal Sci 2017 56(1): 95-97). Five of the IGF-2-treated mice were permanently cured, and their responses to the glucose tolerance test fell between the glucose tolerance results from the literature for non-diabetic obese mice and non-diabetic lean mice. Mouse O1 was not permanently cured, and its glucose levels were higher than the normal obese mouse.

Figure 21:
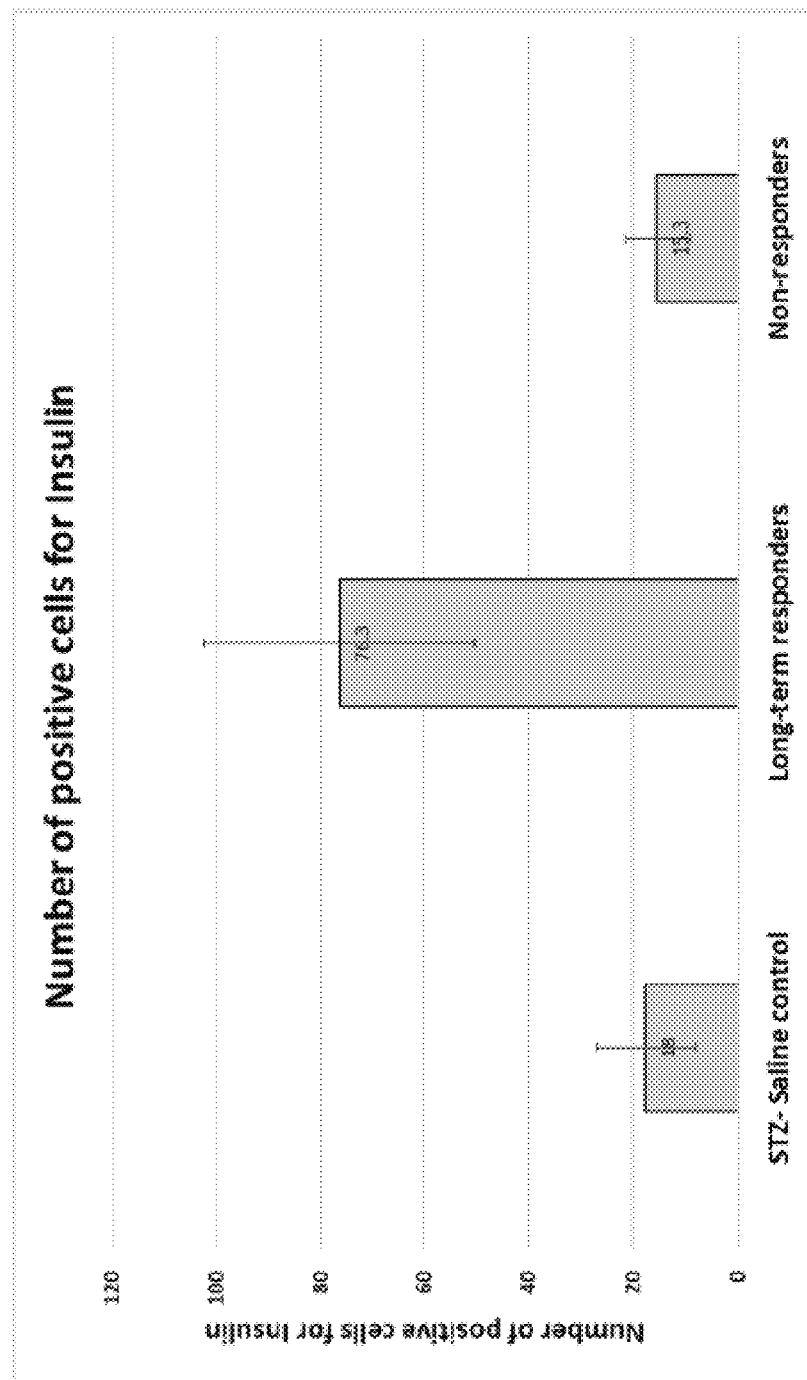
FIG. 21 depicts pancreas histology results on STZ-treated mice.

FIG. 21 depicts pancreas histology results on STZ-treated mice. These results show that treatment using IGF-2 results in a significant increase in the number of cells that test positive for insulin in the permanently cured mice as compared to the non-permanently cured and the control (i.e., saline injection) mice. Permanently cured mice showed an almost four fold increase in the number of functional beta cells. The non-control mice were treated once a day for 10 days with a 3000 µg/kg dose of IGF-2. The mice were sacrificed on day 35 and pancreas cells were assessed as being insulin positive or negative.

Figure 22:
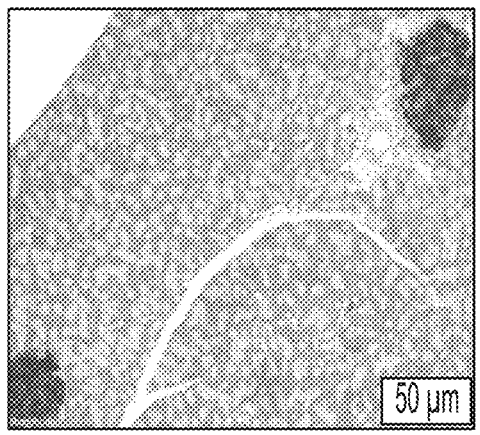
FIG. 22 (upper panels) shows the results of an immunohistochemical staining of pancreas islets for insulin positive cells in STZ-treated mice treated with IGF-2 and the associated glucose response results for the permanently cured and non-permanently cured mice (lower panels)
Figure 22:
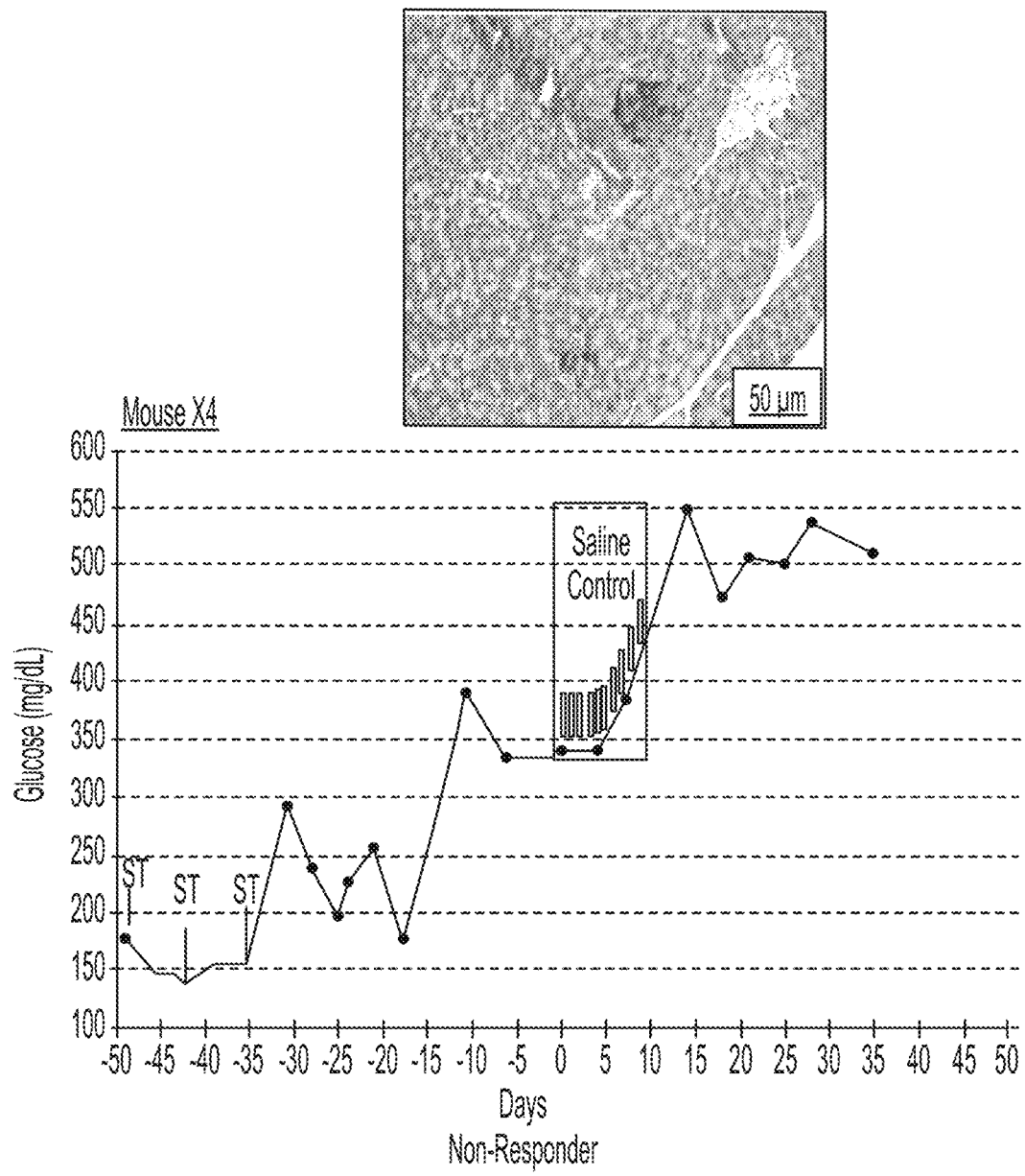
Figure 22:
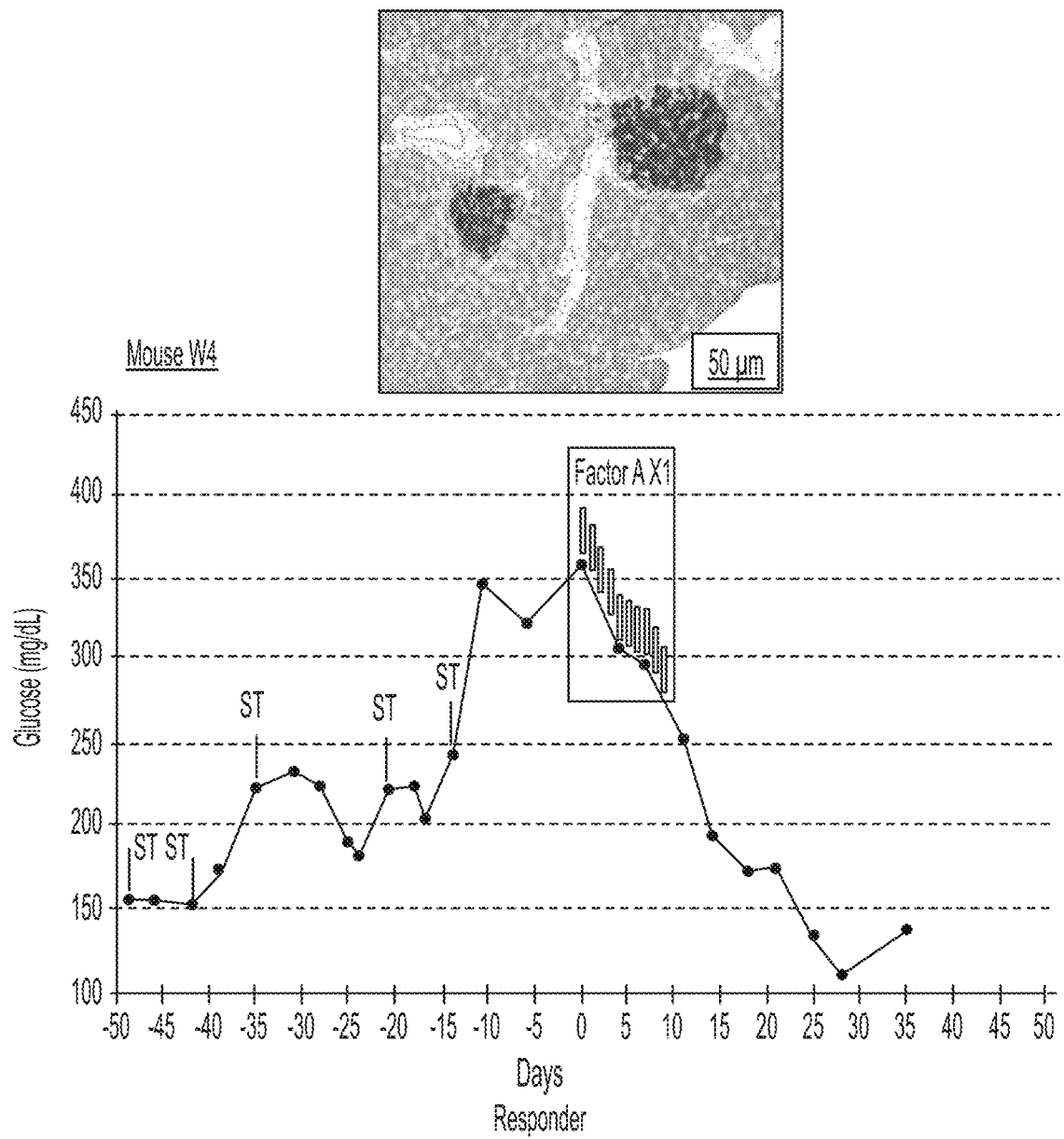

FIG. 22 (upper panels) shows the results of an immunohistochemical staining of pancreas islets for insulin positive cells in STZ-treated mice treated with IGF-2 and for a naive mouse. The staining reveals that the permanently cured mouse had a higher level of insulin in its pancreas islets (as compared to a naïve mouse), while the non-permanently cured mouse had a lower level of insulin in its pancreas islets (as compared to a naïve mouse). This shows that treatment using IGF-2 can result in a recovery of insulin secretion by pancreas islets.

FIG. 22 (lower panels) shows the glucose blood levels for the non-permanently cured mouse and permanently cured mouse. Mice were treated as described for FIG. 21.

Example 10—db/db Mice (Lep$^{db}$)

db/db mice are bred to have a leptin deficiency, increasing susceptibility of the mice to obesity, insulin resistance, and type 2 diabetes (T2D).

Figure 23:
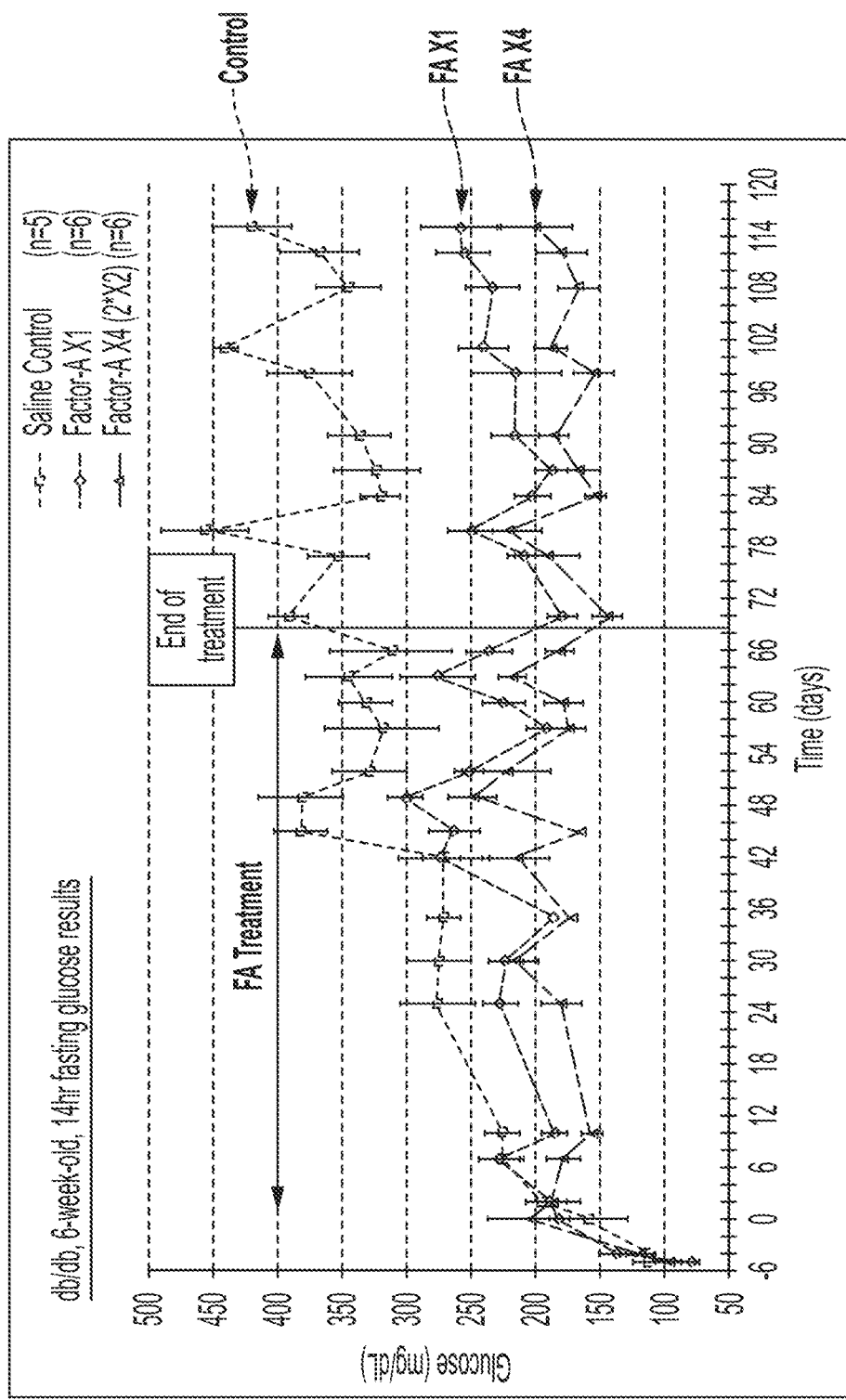
FIG. 23 shows the results of an exemplary experiment on a first group of db/db mice to determine how IGF-2 effects blood glucose levels.

FIG. 23 shows how treating db/db mice with IGF-2 effects blood glucose levels. In this experiment, one group of db/db mice was injected with 3000 μg/kg/day of IGF-2 for 68 days, a second group of db/db mice was injected with 12000 μg/kg/day of IGF-2 for 66 days, and a third group of db/db mice was injected with saline once a day for 68 days. The results show that IGF-2 treatment using either 3000 μg/kg/day or 12000 μg/kg/day reduced blood glucose levels (14 hour fasting blood glucose levels) to a normal range even after the end of the 68 day treatment period.

Figure 24:
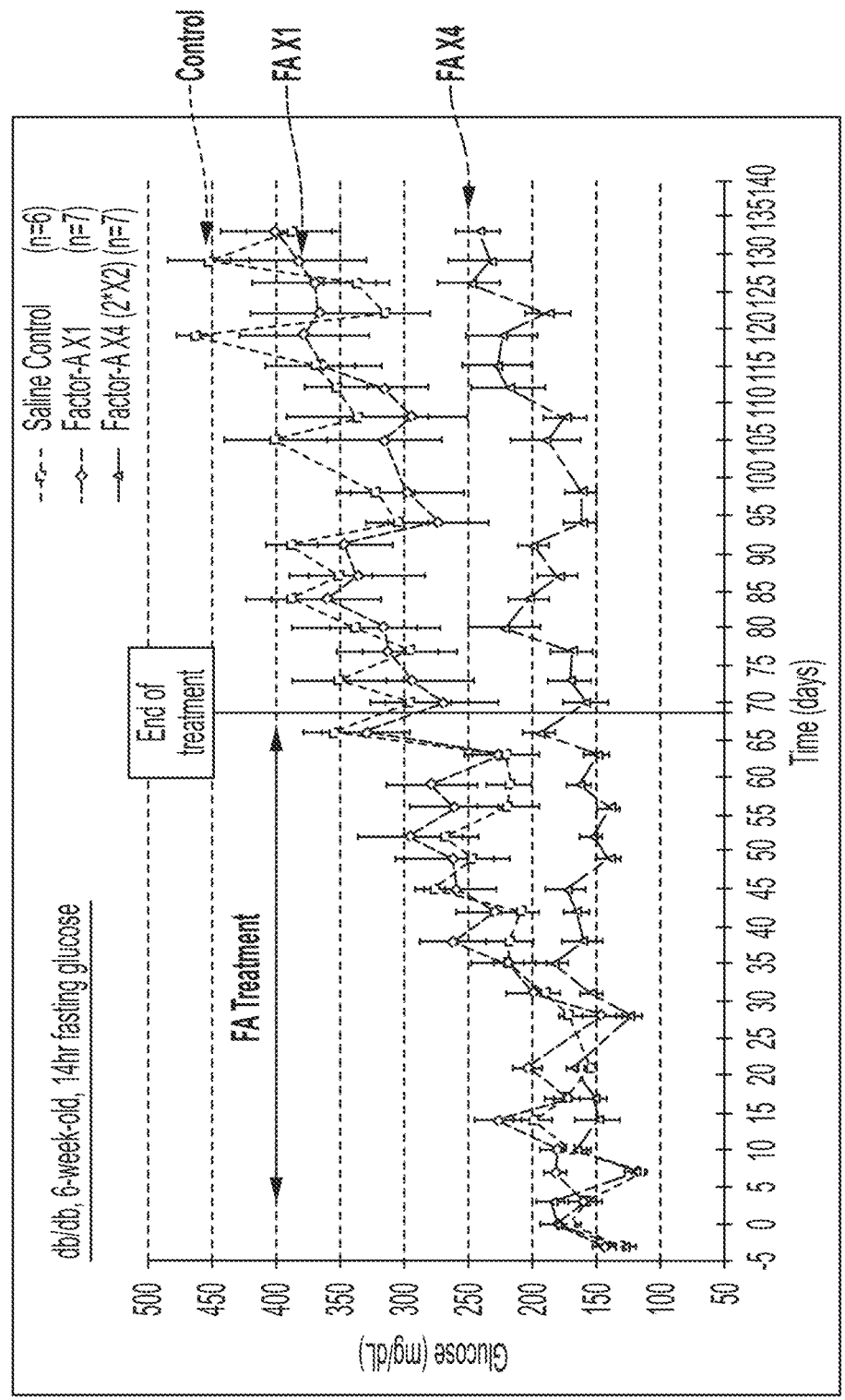
FIG. 24 shows the results of an exemplary experiment on a second group of db/db mice to determine how IGF-2 effects blood glucose levels.

FIG. 24 shows the results of an experiment similar to the experiment of FIG. 23 in a second group of db/db mice. The results show that IGF-2 treatment using 12,000 μg/kg/day reduced blood glucose levels (14 hour fasting blood glucose levels) to a normal range even after the end of the 68 day treatment period. But in this iteration of the experiment, the blood glucose levels of the 3000 μg/kg/day group were not reduced with respect to the control. This indicates that a daily dose larger than 3000 μg/kg can be preferable, and that daily doses of at least 12,000 μg/kg can provide better results.

Figure 25:
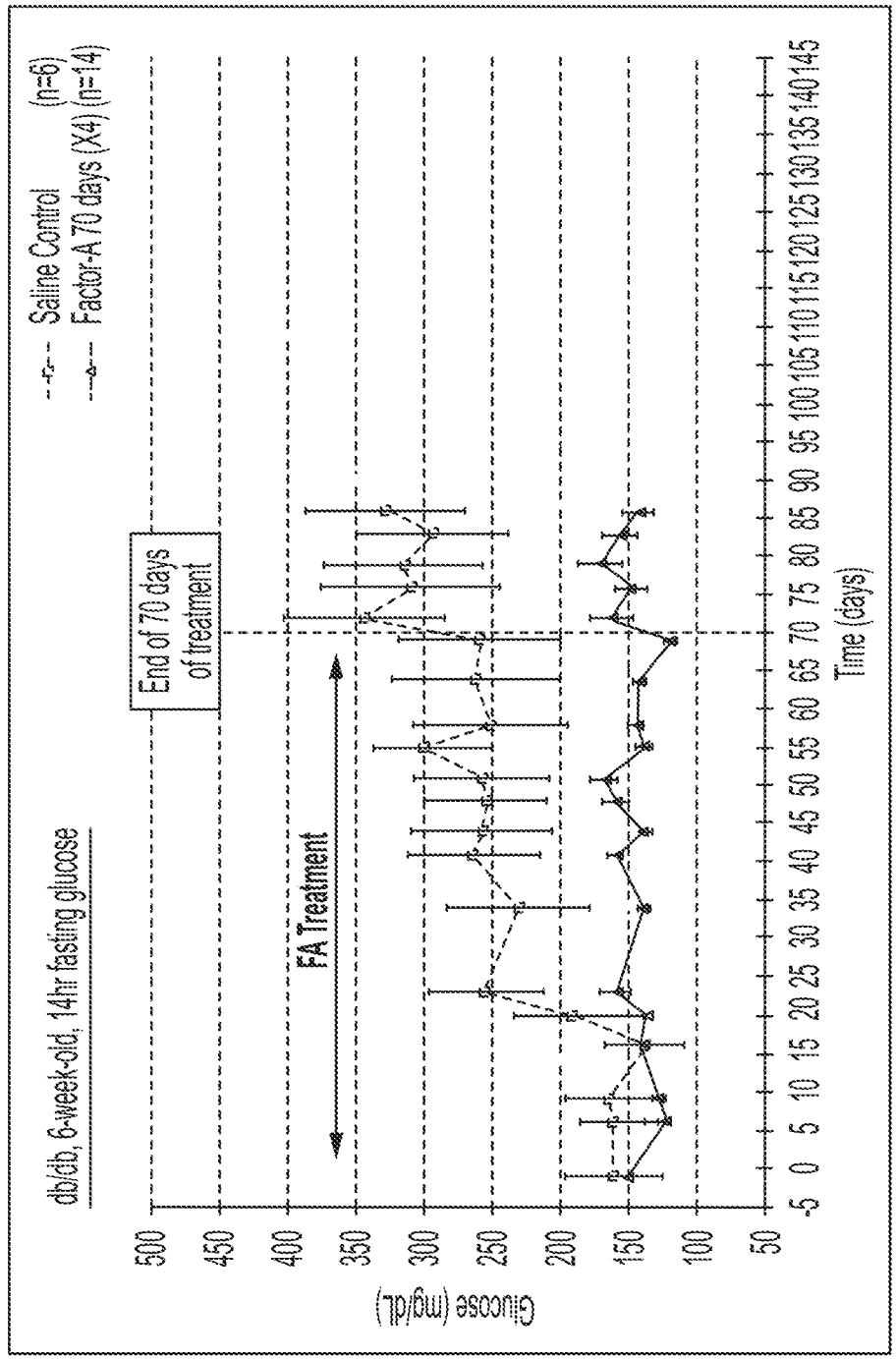
FIG. 25 shows the results of an exemplary experiment on a third and fourth groups of db/db mice to determine how IGF-2 effects blood glucose levels.
Figure 25:
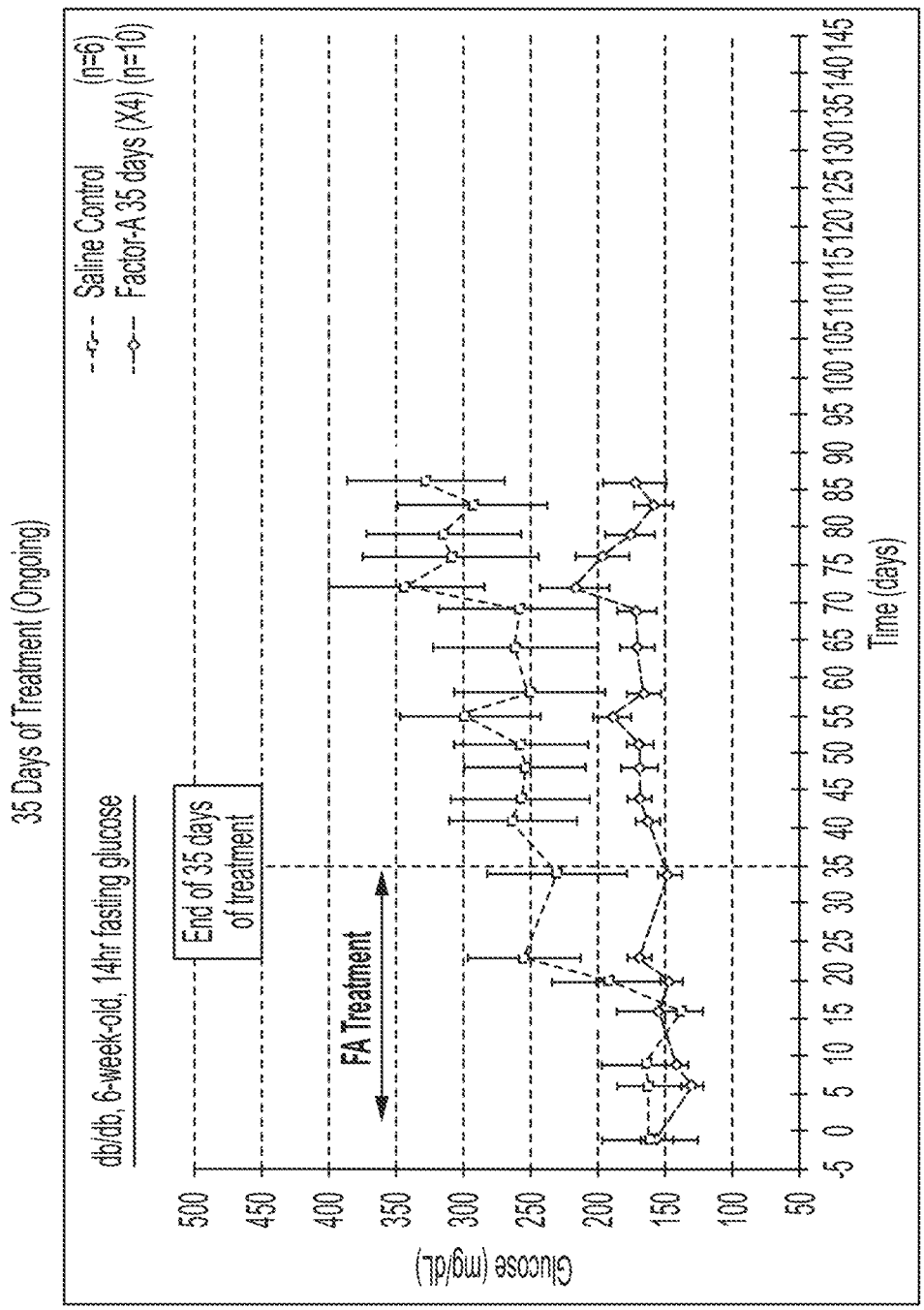

FIG. 25 shows the results of two additional experiments in which db/db mice were treated with IGF-2. In one experiment (left panel), one group of db/db mice was injected with a daily dose of 12000 μg/kg of IGF-2 divided in two injections per day for 70 days, while another group of db/db mice was injected with saline. The results show that IGF-2 treatment using 12000 μg/kg/day reduced blood glucose levels (14 hour fasting blood glucose levels) to a normal range even after the end of the 70 day treatment period. In another experiment (right panel), one group of db/db mice was injected with a daily dose of 12000 μg/kg of IGF-2 divided in two injections per day for 35 days, while another group of db/db mice was injected with saline. The results show that IGF-2 treatment using 12000 μg/kg/day reduced blood glucose levels (14 hour fasting blood glucose levels) to a normal range even after the end of the 35 day treatment period.

Figure 26:
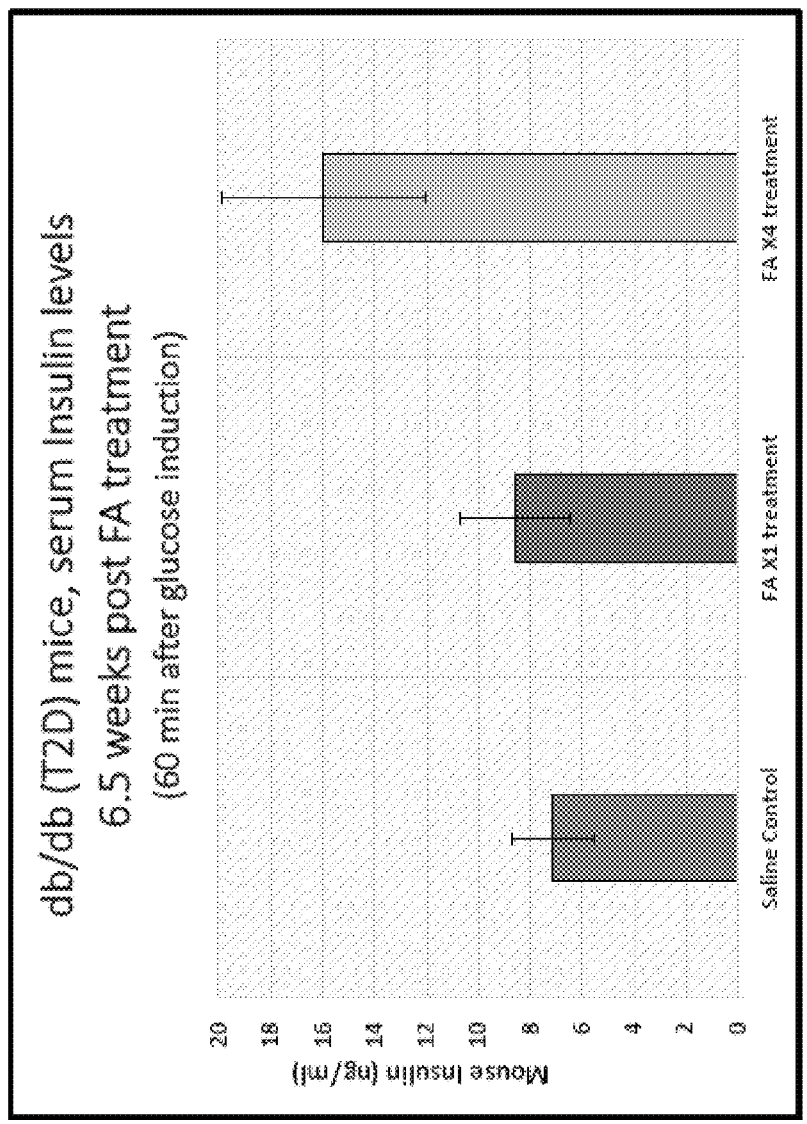
FIG. 26 shows the results of an exemplary experiment that demonstrates how long-term treatment with IGF-2 enhances the levels of serum insulin in db/db mice.

FIG. 26 shows how long-term treatment with IGF-2 enhances the levels of serum insulin in db/db mice. In this experiment, one group of db/db mice (labeled FA X1) was injected with 3000 μg/kg of IGF-2 once a day for 68 days, a second group of db/db mice (labeled FA X4) was injected with a daily dose of 12000 μg/kg of IGF-2 divided in two injections per day for 68 days, and a third group of db/db mice was injected with saline. Serum insulin levels were measured 6.5 weeks after the end of the 68 day treatment. Treatment with the 12,000 μg/kg daily dose increased serum insulin levels by about 50% with respect to the control.

Figure 27:
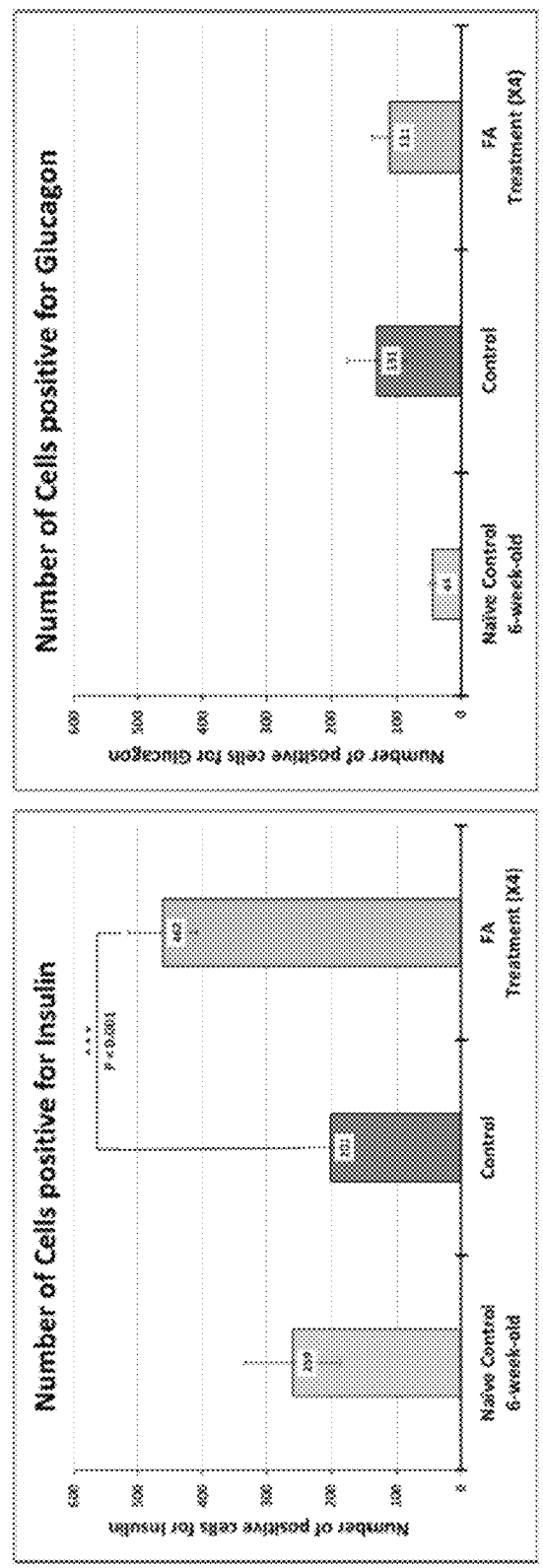
FIG. 27 provides exemplary histopathology results showing the number of pancreas islet cells that test positive for insulin and glucagon after treating db/db mice with IGF-2.

FIG. 27 provides results of histopathology and immunohistochemical studies showing the number of pancreas islet cells that test positive for insulin (left panel) and glucagon (right panel) in db/db mice. In this experiment, one group of db/db mice was injected with 12000 μg/kg of IGF-2 on each of 70 consecutive days, a second group of db/db mice was injected with saline, and a third group of db/db mice was a naïve control group. The mice were sacrificed for pathology 70 days after the end of the initial 70 day treatment. The results show a more than 50% increase in the number of insulin-positive cells, which indicates beta cell proliferation. Evidence obtained thus far does not support the assumption that the increase in the number of insulin-positive results from trans-differentiation of glucagon-secreting alpha cells into beta cells.

Figure 28:
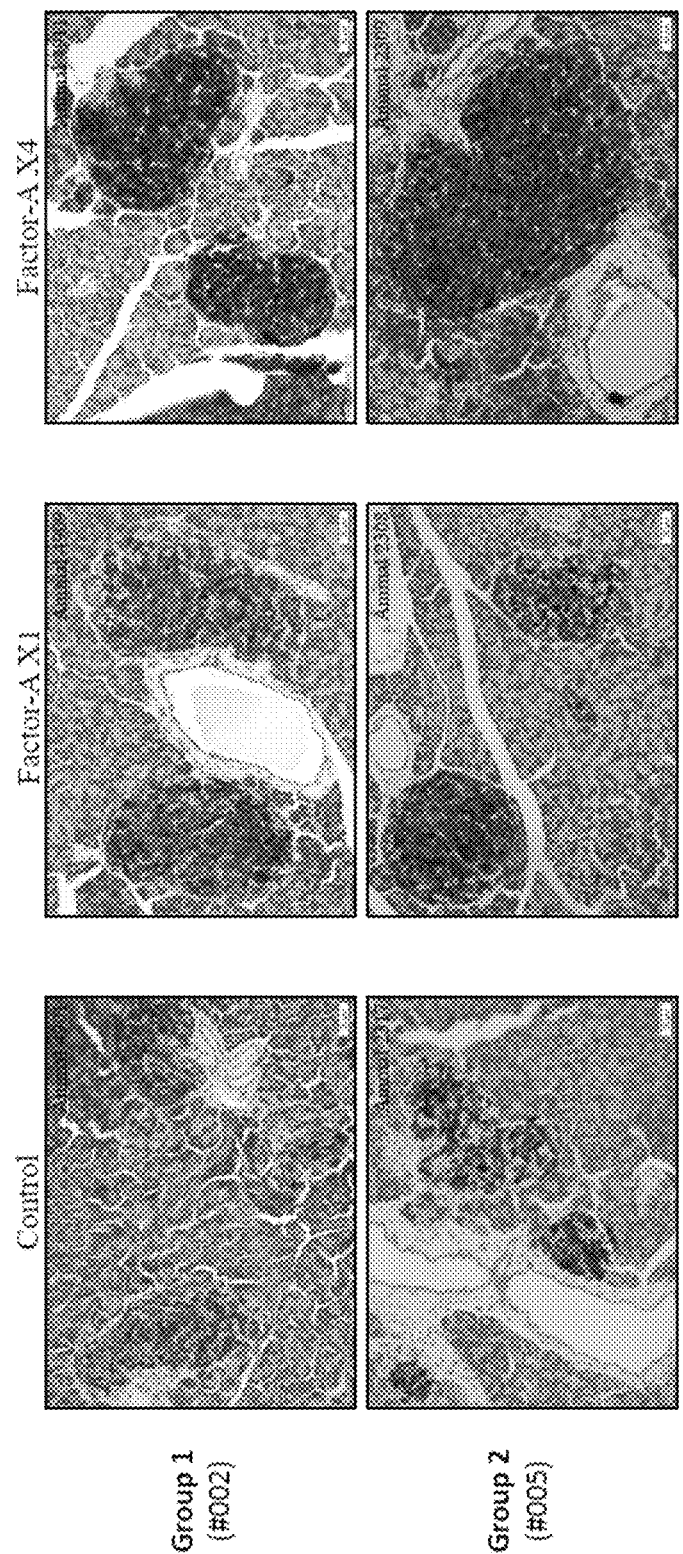
FIG. 28 shows the results of an immunohistochemical staining of pancreas islets for insulin positive cells in db/db mice treated with IGF-2.

FIG. 28 shows immunohistochemical staining of pancreas islet cells from db/db mice. In this experiment, one group of db/db mice (labeled X4) was injected with 12000 μg/kg of IGF-2 on each of 70 consecutive days, a second group of db/db mice (labeled X1) was injected with 3000 μg/kg of IGF-2 on each of 70 consecutive days, and a third group of db/db mice (labeled control) was injected with saline. The mice were sacrificed for pathology 70 days after the end of the initial 70 day treatment. These images show an increase in insulin positive cells in a dose-dependent manner. The control panels show a positive stain for insulin, which increases in intensity in the 3000 μg/kg/day mice, and increases again in intensity in the 12,000 μg/kg/day mice. Taken together, these data show that IGF-2 can be used to treat type 2 diabetes or prevent onset of type 2 diabetes in prediabetic subjects.

Example 11—Non-Obese Diabetic (NOD) Mice

Non-Obese Diabetic (NOD) mice are a polygenic model for spontaneous autoimmune type 1 diabetes (T1D). NOD mice have an elevated risk for development of autoimmune type 1 diabetes. Thus, NOD mice were used to determine whether treatment IGF-2 reduces spontaneous development of type 1 diabetes.

Figure 29:
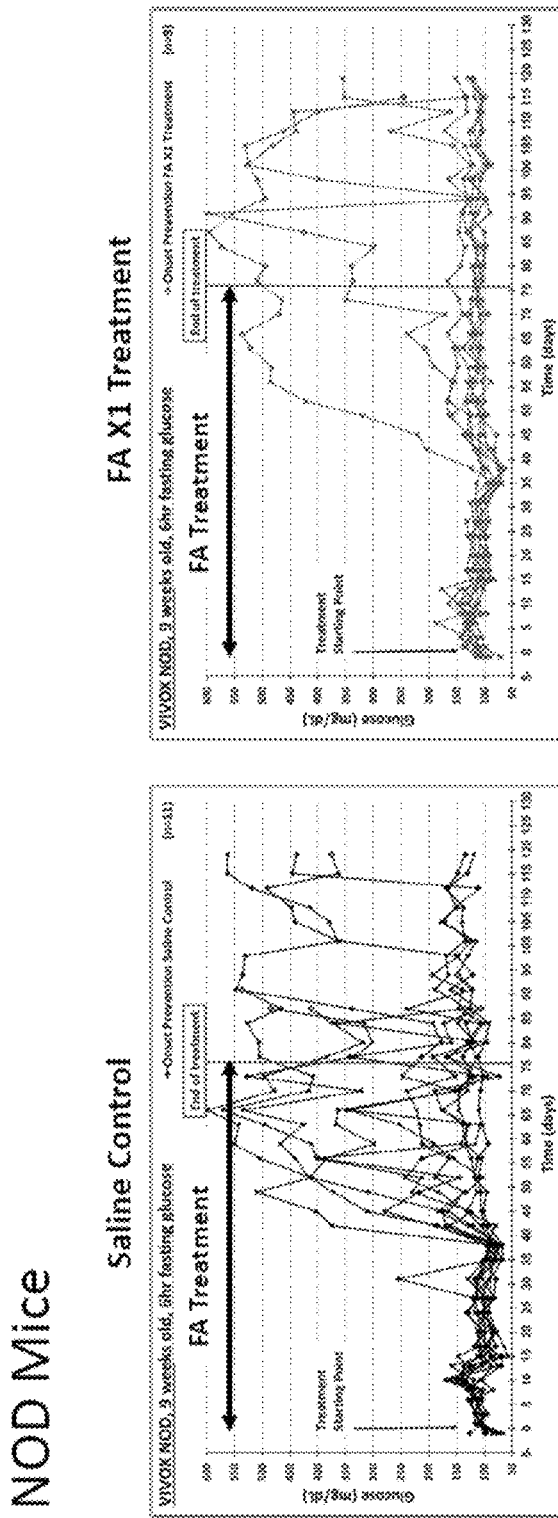
FIG. 29 shows the results of an experiment to determine how IGF-2 effects the onset of type 1 diabetes in NOD mice.

FIG. 29 shows the effects of IGF-2 treatment on the incidence of spontaneous autoimmune attack/type 1 diabetes in NOD mice. In this experiment, one group of NOD mice (right panel) was injected with 3000 μg/kg of IGF-2 on each of 76 consecutive days, and a second group of NOD mice (left panel) was injected with saline. The results show that the incidence of spontaneous autoimmune attack was reduced dramatically by the IGF-2 treatment. More specifically, at the end of the 76 days of treatment, only two of the treated mice had developed high glucose levels.

Figures 30A, 30B:
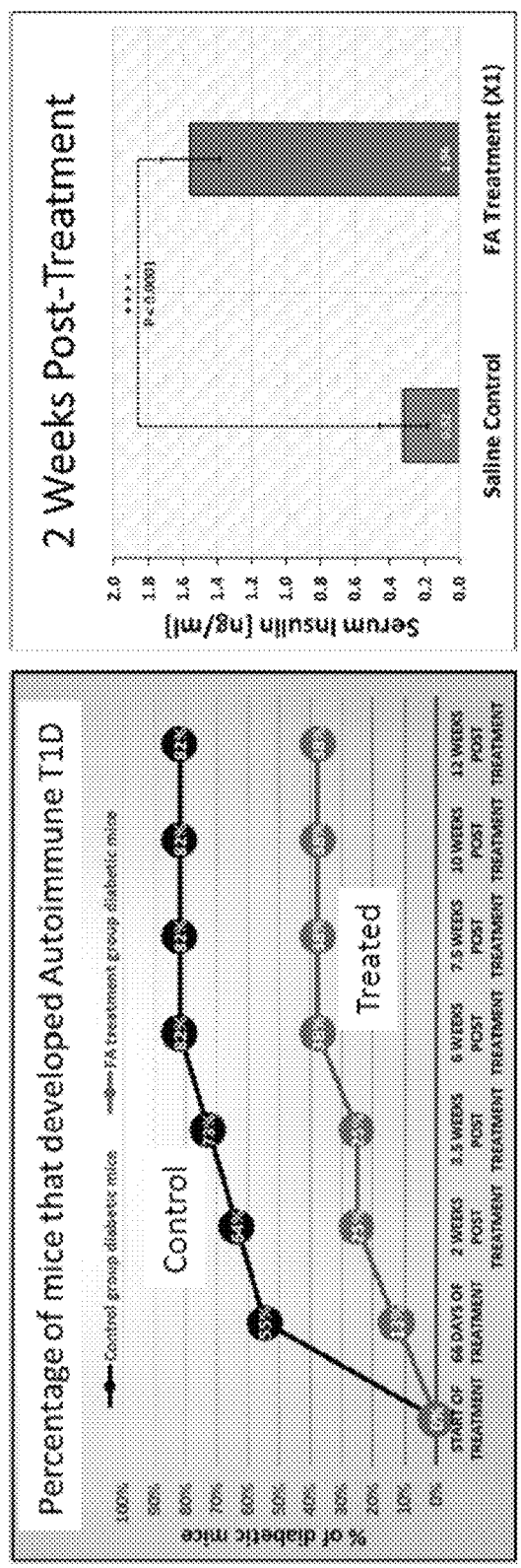
FIG. 30A shows the results of another experiment to determine how IGF-2 effects the onset of type 1 diabetes in NOD mice.
FIG. 30B shows the serum insulin levels two weeks following treatment with IGF-2.

FIG. 30A depicts how many NOD mice have developed autoimmune type I diabetes during an initial 66 days of treatment with IGF-2, and at various intervals post-treatment. In this experiment, one group of NOD mice was injected with 3000 μg/kg of IGF-2 on each of 66 consecutive days, and a second group of NOD mice was injected with saline. The incidence of spontaneous autoimmune type 1 diabetes was significantly reduced in the treated mice with respect to the control.

FIG. 30B depicts the levels of serum insulin in NOD mice measured two weeks after a 66 day course of treatment using IGF-2. Mice that were treated with 3000 μg/kg/day of IGF-2 had serum insulin levels that were about 4-fold higher than the control mice. Taken together, these results show that IGF-2 can be used to prevent onset of type I diabetes.

In another experiment, NOD mice were untreated or treated with IGF-2. In this experiment, the untreated NOD mice showed complete destruction of islet cells due to autoimmune attack, as evidenced by the complete lack of histological staining for insulin, and the relatively small amount of histological staining for glucagon. In contrast, NOD mice treated with IGF-2 for 13 weeks had fully functional islet cells as indicated by significant histological staining for both glucagon and insulin.

The results described in the previous paragraph were confirmed by comparing the number of cells staining positive for insulin in NOD mice treated with IGF-2 versus untreated NOD mice.

Example 12—In Vitro Experiments in β-MIN6 Cells

β-MIN6 cells serve as an in vitro model of mouse pancreatic islets. β-MIN6 cells were used as an in vitro model to measure the effects of treatment with IGF-2.

Figure 31:
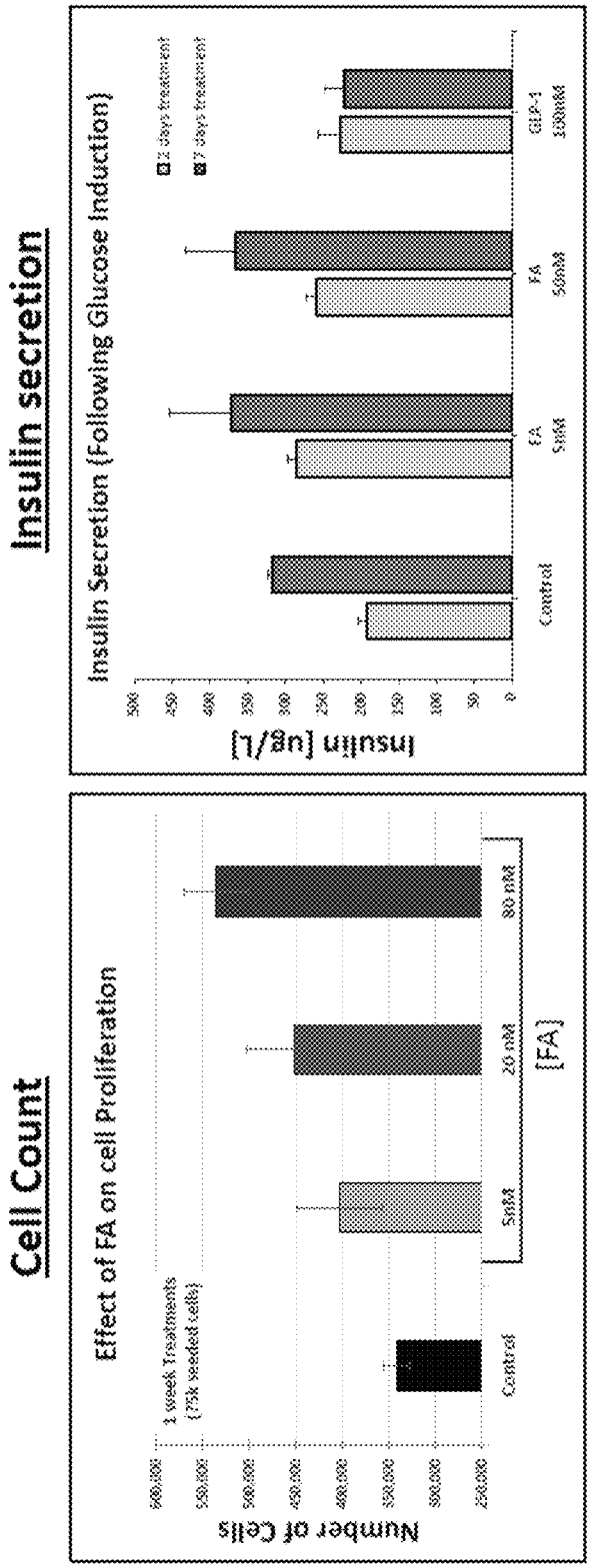
FIG. 31 illustrates the effects of various levels of IGF-2 on cell proliferation and insulin secretion following glucose induction in vitro.

FIG. 31 shows the effects of IGF-2 on cell count (e.g., cell proliferation) and insulin secretion at three different concentrations (5 nM, 20 nM, 80 nM) on β-MIN6 cells compared to control, untreated β-MIN6 cells.

The left panel of FIG. 31 shows that IGF-2 increases cell proliferation in a dose-dependent manner after a 1 week treatment at the three measured concentrations. The right panel of FIG. 31 shows that IGF-2 also increases insulin secretion (following glucose induction) in a dose-dependent manner after a 1 week treatment. GLP-1 (a satiety hormone) does not increase insulin secretion (right panel). The results confirm the in vivo results discussed above and show that IGF-2 can increase the number of cells and insulin secretion.

Figure 32:
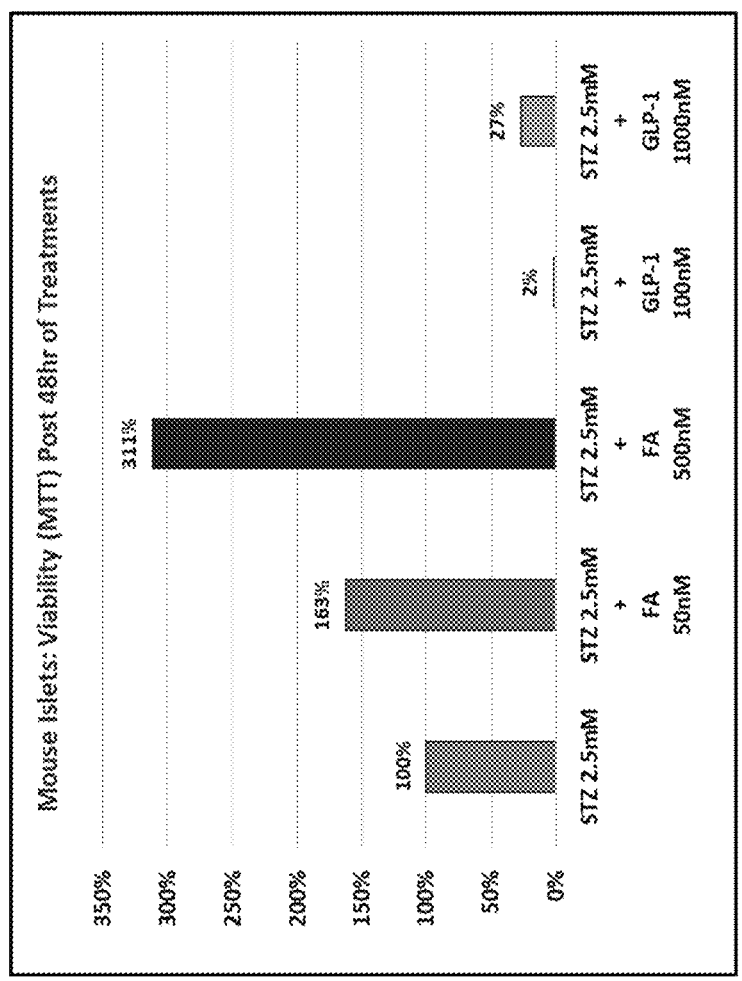
FIG. 32 illustrates the viability of STZ-treated mouse islet cells using MTT stain following treatment with IGF-2 compared to treatment with GLP-1.

FIG. 32 shows the effects of IGF-2 on normal mouse islet cell viability using an MTT [3-(4,5-dimethylthiazol-2-yl)-2,5-diphenyltetrazolium bromide] dye in STZ-treated mouse islets. Yellow dye MTT is converted to a purple dye by mitochondrial reductase in viable cells. Therefore, the amount of purple dye present determined by measuring optical density of cells at 570 nm serves as a measurement of cell viability. As shown in FIG. 32, mouse islet viability increased in a dose dependent manner with increasing concentrations of IGF-2. In contrast, GLP-1 (a satiety hormone) did not significantly increase mouse islet viability.

Another experiment was performed to show the effects of IGF-2 on insulin secretion from STZ-treated mouse islets 48 hours after treatment IGF-2. Mouse islet cells were treated with 2.5 mM STZ and subsequently treated with either IGF-2 (FA) at 50 nM and 500 nM, or with GLP-1 at 100 nM and 1000 nM. The results were as follows: insulin secretion increased in a dose dependent manner with increasing concentrations of IGF-2. In contrast, GLP-1 (a satiety hormone) did not significantly increase insulin secretion.

Figure 33:
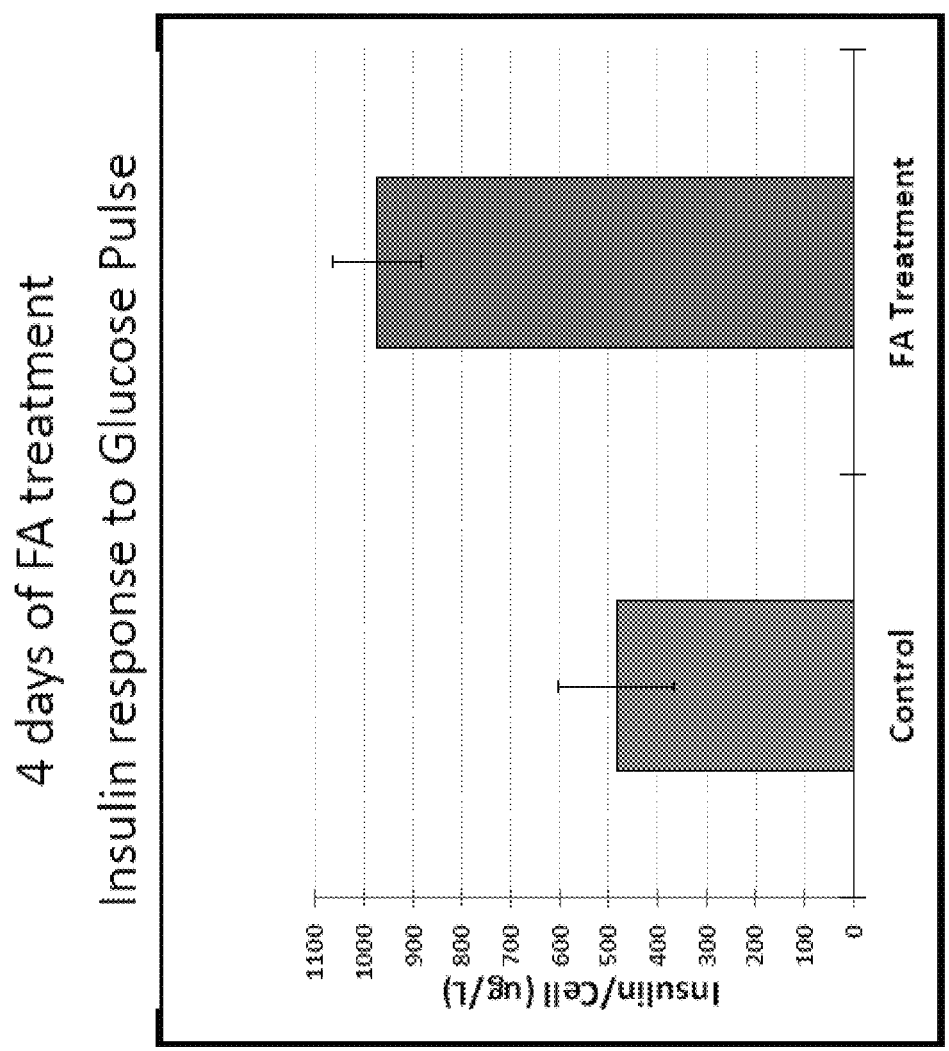
FIG. 33 shows how treatment with IGF-2 changes the insulin response to a glucose pulse in human pancreatic islet cells.

FIG. 33 shows the effects of IGF-2 in vitro on human pancreatic islet cells. As shown in FIG. 33, treating human pancreatic islet cells with IGF-2 at a concentration of 50 nM for four days increased insulin secretion in response to a glucose pulse by nearly 50% compared to untreated human pancreatic islet cells.

Example 13—Management and Treatment of Diabetes with IGF-2

As described herein, IGF-2 and variants thereof can be used to manage or cure diabetes. Short-term effects include lowering blood glucose in hyperglycemic subjects and supplementing insulin secretion due to lack of sufficient functional beta cell mass.

IGF-2 and variants thereof can also be used to provide at least the following long-term benefits: (1) lowering blood glucose levels in patients diagnosed with type 2 diabetes, (2) relieving beta cell insulin secretion stress, (3) delaying or prevent onset of type 1 diabetes, and (4) maintaining normoglycemia.

Example 14—Treatment of NOD with IGF-2

In one exemplary experiment, NOD mice were treated with a 3000 µg/kg daily doses of IGF-2 for 150 days. 4/5 of the treated mice maintained normoglycemia compared to 1/4 of the control mice. In another exemplary experiment, NOD mice were treated with a 3000 µg/kg daily dose of IGF-2 for 75 days with follow-up glucose measurements taken for an additional 90 days (during which IGF-2 was not administered). 5/8 of the treated mice maintained normoglycemia compared to 2/11 of the control mice. The average insulin secretion of the treated mice in both of these experiments was five times greater than the control mice.

Example 15—Treatment of db/db Mice

In one exemplary experiment, db/db mice were treated with a 12,000 µg/kg daily dose for 70 days with 70 days of follow up (during which IGF-2 was not administered). All the treated mice maintained normoglycemia for at least 50 days following treatment. In another exemplary experiment, db/db mice were treated with a 12,000 µg/kg daily dose for 35 days with 35 days of follow up (during which IGF-2 was not administered). All the treated mice maintained normoglycemia for 35 days following treatment.

Example 16—Summary of Safety/Toxicity

No pathologies were identified related to treatment in blood samples, and tissue samples from thirty organs (pancreas, liver, etc.) at the end of 10 days of treatment with IGF-2, 24 days after termination of IGF-2 treatment, and 100 days after termination of 30 days of treatment with IGF-2.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of treating Type 1 or Type 2 diabetes in a subject in need of treatment, the subject having a weight, the method comprising: administering first, second, third, fourth, and fifth daily doses of insulin like growth factor 2 (IGF-2) to the subject at respective first, second, third, fourth, and fifth different days, wherein each of the daily doses comprises 65 μg to 1626 μg of IGF-2 thereof per kg of the weight.

2. The method of claim 1, wherein the first, second, third, fourth, and fifth different days occur on consecutive days.

3. The method of claim 1, further comprising administering sixth, seventh, and eighth daily doses of IGF-2 to the subject at respective sixth, seventh, and eighth different days.

4. The method of claim 1, further comprising administering sixth, seventh, eighth, ninth, and tenth daily doses of IGF-2 to the subject at respective sixth, seventh, eighth, ninth, and tenth different days, wherein the first, second, third, fourth, fifth, sixth, seventh, eighth, ninth, and tenth different days occur on consecutive days.

5. The method of claim 1, wherein each of the daily doses comprises at least 163 μg of IGF-2 per kg of the weight.

6. The method of claim 1, wherein each of the daily doses comprises at least 244 μg of IGF-2 per kg of the weight.

7. The method of claims 1, wherein each of the daily doses comprises at least 813 μg of IGF-2 per kg of the weight.

* * * * *